United States Patent [19]

Burton et al.

[11] Patent Number: 5,716,948
[45] Date of Patent: Feb. 10, 1998

[54] 3-SUBSTITUTED CARBACEPHEMS

[75] Inventors: George Burton, Wallington; Antoinette Naylor, Woking, both of England

[73] Assignee: Pfizer Inc., New York, N.Y.

[21] Appl. No.: 351,278

[22] PCT Filed: May 26, 1993

[86] PCT No.: PCT/GB93/01092

§ 371 Date: Dec. 7, 1994

§ 102(e) Date: Dec. 7, 1994

[87] PCT Pub. No.: WO93/25551

PCT Pub. Date: Dec. 23, 1993

[30] Foreign Application Priority Data

Jun. 13, 1992 [GB] United Kingdom .......... 9212609

[51] Int. Cl.$^6$ .......... C07D 463/10; A61K 31/33
[52] U.S. Cl. .......... 514/210; 540/205
[58] Field of Search .......... 540/205; 514/210

[56] References Cited

U.S. PATENT DOCUMENTS 5,246,926  9/1993  Batesan et al. .......... 514/202

FOREIGN PATENT DOCUMENTS

WO 92/01696  2/1992  WIPO .
WO 92/01695  2/1992  WIPO .

*Primary Examiner*—John M. Ford
*Attorney, Agent, or Firm*—Peter C. Richardson; Paul H. Ginsburg; Lorraine B. Ling

[57] ABSTRACT

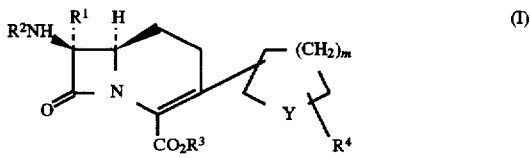

A compound of formula (I) or a salt thereof, wherein $R^1$ is hydrogen, methoxy or formamido; $R^2$ is an acyl group, in particular that of an antibacterially active cephalosporin; $CO_2R^3$ is a carboxy group or a carboxylate anion, or $R^3$ is a readily removable carboxy protecting group or a pharmaceutically acceptable salt-forming group or in vivo hydrolysable ester group; $R^4$ represents hydrogen or up to four substituents, which may be present on any of the carbon atoms in the ring system shown, selected from alkyl, alkenyl, alkynyl, alkoxy, hydroxy, halogen, amino, alkylamino, acylamino, dialkylamino, $CO_2R$, $CONR_2$, $SO_2NR_2$ where R is hydrogen or alkyl, aryl and heterocyclyl, which may be the same or different and wherein any $R^4$ alkyl substituent is optionally substituted by one or more substituents selected from the list from which $R^4$ is selected; Y is O, S, SO or $SO_2$; and m is 1 or 2, a process for its preparation, use as an antibiotic and intermediates thereto.

10 Claims, No Drawings

3-SUBSTITUTED CARBACEPHEMS

This a 371 of PCT/GB93/01092 filed May 26, 1993.

This invention relates to novel β-lactam compounds, their preparation and their use, and in particular to a novel class of cephems. These compounds have antibacterial properties, and are therefore of use in the treatment of bacterial infections in humans and animals caused by a wide range of organisms.

PCT/GB91/01228 (WO 92/01696) genetically discloses cephems of general formula (A):

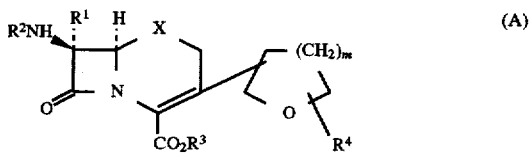

wherein $R^1$, $R^2$, $R^3$ and $R^4$ are various substituents, m is 1 or 2 and X is S, SO, $SO_2$, O or $CH_2$.

We have found a particularly advantageous class of carbacephems bearing a cyclic ether or thio-ether substituent at the 3-position of the cephem nucleus, and which are not specifically disclosed in WO92/01696.

The present invention provides a compound of formula (I) or a salt thereof:

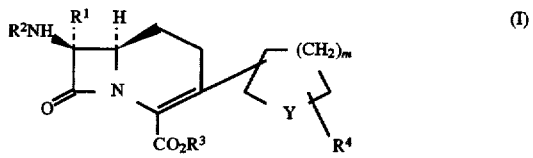

wherein:

$R^1$ is hydrogen, methoxy or formamido;

$R^2$ is an acyl group, in particular that of an antibacterially active cephalosporin;

$CO_2R^3$ is a carboxy group or a carboxylate anion, or $R^3$ is a readily removable carboxy protecting group or a pharmaceutically acceptable salt-forming group or in vivo hydrolysable ester group;

$R^4$ represents hydrogen or up to four substituents, which may be present on any of the carbon atoms in the ring system shown, selected from alkyl, alkenyl, alkynyl, alkoxy, hydroxy, halogen, amino, alkylamino, acylamino, dialkylamino, $CO_2R$, $CONR_2$, $SO_2NR_2$ where R is hydrogen or alkyl, aryl and heterocyclyl, which may be the same or different and wherein any $R^4$ alkyl substituent is optionally substituted by one or more substituents selected from the list from which $R^4$ is selected;

Y is O, S, SO or $SO_2$; and m is 1 or 2.

The bonding carbon atom of the cyclic ether or thio-ether moiety which links the ring to the cephem nucleus is generally asymmetric. The present invention includes either stereoisomer, as well as mixtures of both isomers.

In compounds of formula (I) wherein $R^1$ is formamido, the formamido group can exist in conformations wherein the hydrogen atoms of the —NH—CHO moiety are cis- or trans-; of these the cis conformation normally predominates.

Preferred compounds within formula (1) are compounds of formula (Ia) or pharmaceutically acceptable salts or pharmaceutically acceptable in vivo hydrolysable esters thereof:

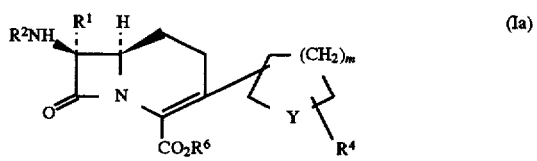

wherein $R^1$, $R^2$, $R^4$, m and y are as defined with respect to formula (I) and the group $CO_2R^6$ is $CO_2R^3$ where $CO_2R^3$ is a carboxy group or a carboxylate anion.

Accordingly, the present invention provides a compound of formula (Ia) or a pharmaceutically acceptable salt or in vivo hydrolysable ester thereof, for use as a therapeutic agent, and in particular an in vivo hydrolysable ester thereof for use as an orally administrable therapeutic agent.

The present invention further provides a compound of formula (Ia) or a pharmaceutically acceptable salt or in vivo hydrolysable ester thereof, for use in the treatment of bacterial infections, more particularly an in vivo hydrolysable ester thereof for use in the oral treatment of bacterial infections.

The present invention also includes a method of treating bacterial infections in humans and animals which comprises the administration of a therapeutically effective amount of an antibiotic compound of the formula (Ia) or a pharmaceutically acceptable in vivo hydrolysable ester thereof, in particular the oral administration of a therapeutically effective amount of an in vivo hydrolysable ester.

In addition, the present invention includes the use of a compound of formula (Ia) or a pharmaceutically acceptable salt or in vivo hydrolysable ester thereof, for the manufacture of a medicament for the treatment of bacterial infections, in particular the use of an in vivo hydrolysable ester for the manufacture of a medicament for the oral treatment of bacterial infections.

Those compounds of the formula (I) wherein $R^3$ is a readily removable carboxy protecting group other than a pharmaceutically acceptable in vivo hydrolysable ester or which are in non-pharmaceutically acceptable salt form are primarily useful as intermediates in the preparation of compounds of the formula (Ia) or a pharmaceutically acceptable salt or pharmaceutically acceptable in vivo hydrolysable ester thereof.

Suitable readily removable carboxy protecting groups for the group $R^3$ include groups forming ester derivatives of the carboxylic acid, including in vivo hydrolysable esters. The derivative is preferably one which may readily be cleaved in vivo.

Also included within the scope of the invention are salts and carboxy-protected derivatives, including in vivo hydrolysable esters, of any carboxy groups that may be present as optional substituents in compounds of formula (1) or (Ia). Also included within the scope of the invention are acid addition salts of any amino group or substituted amino group that may be present as optional substituents in compounds of formula (I) or (Ia).

Suitable ester-forming carboxyl-protecting groups are those which may be removed under conventional conditions. Such groups for $R^3$ include benzyl, p-methoxybenzyl, benzoylmethyl, p-nitrobenzyl, 4-pyridylmethyl, 2,2,2-trichloroethyl, 2,2,2-tribromoethyl, t-butyl, t-amyl, allyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, acetonyl, p-toluenesulphonylethyl, methoxymethyl, 2-trimethylsilylethyl, a silyl, stannyl or phosphorus- containing group, an oxime radical of formula —N=$CHR^7$ where $R^7$ is aryl or heterocyclic, or an in vivo hydrolysable ester radical such as defined below.

A carboxyl group may be regenerated from any of the above esters by usual methods appropriate to the particular $R^3$ group, for example, acid- and base-catalysed hydrolysis, or by enzymically-catalysed hydrolysis, or by hydrogenolysis under conditions wherein the remainder of the molecule is substantially unaffected.

Examples of suitable pharmaceutically acceptable in vivo hydrolysable ester groups include those which break down readily in the human body to leave the parent acid or its salt. Suitable ester groups of this type include those of part formulae (i), (ii), (iii), (iv) and (v):

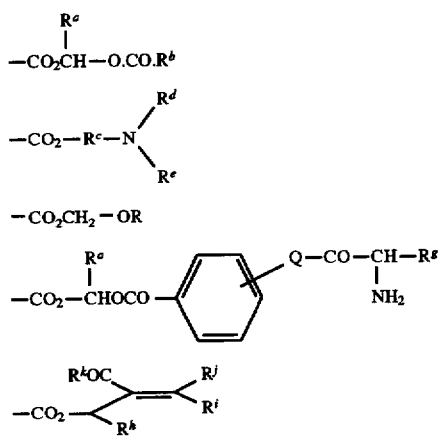

wherein $R^a$ is hydrogen, $(C_{1-6})$ alkyl, $(C_{3-7})$ cycloalkyl, methyl, or phenyl, $R^b$ is $(C_{1-6})$ alkyl, $(C_{1-6})$ alkoxy, phenyl, benzyl, $(C_{3-7})$ cycloalkyl, $(C_{3-7})$ cycloalkyloxy, $(C_{1-6})$ alkyl $(C_{3-7})$ cycloalkyl, 1-amino $(C_{1-6})$ alkyl, or 1-$((C_{1-6})$ alkyl) amino $(C_{1-6})$ alkyl; or $R^a$ and $R^b$ together form a 1,2-phenylene group optionally substituted by one or two methoxy groups; $R^c$ represents $(C_{1-6})$ alkylene optionally substituted with a methyl or ethyl group and $R^d$ and $R^e$ independently represent $(C_{1-6})$ alkyl; $R^f$ represents $(C_{1-6})$ alkyl; $R^g$ represents hydrogen or phenyl optionally substituted by up to three groups selected from halogen, $(C_{1-6})$ alkyl, or $(C_{1-6})$ alkoxy; Q is oxygen or NH; $R^h$ is hydrogen or $(C_{1-6})$ alkyl; $R^i$ is hydrogen, $(C_{1-6})$ alkyl optionally substituted by halogen, $(C_{2-6})$ alkenyl, $(C_{1-6})$ alkoxycarbonyl, aryl or heteroaryl; or $R^h$ and $R^i$ together form $(C_{1-6})$ alkylene; $R^j$ represents hydrogen, $(C_{1-6})$ alkyl or $(C_{1-6})$ alkoxycarbonyl; and $R^k$ represents $(C_{1-8})$ alkyl, $(C_{1-8})$ alkoxy, $(C_{1-6})$ alkoxy$((C_{1-6}))$alkoxy or aryl.

Examples of suitable in vivo hydrolysable ester groups include, for example, acyloxyalkyl groups such as acetoxymethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; alkoxycarbonyloxy-alkyl groups, such as ethoxycarbonyloxymethyl, α-ethoxycarbonyloxyethyl and propoxycarbonyloxyethyl; dialkylaminoalkyl especially di-loweralkylamino alkyl groups such as dimethylaminomethyl, dimethylaminoethyl, diethylaminomethyl or diethylaminoethyl; 2-(alkoxycarbonyl)-2-alkenyl groups such as 2-(isobutoxycarbonyl)pent-2-enyl and 2-(ethoxycarbonyl) but-2-enyl; lactone groups such as phthalidyl and dimethoxyphthalidyl; and esters linked to a second β-lactam antibiotic or to a β-lactamase inhibitor.

A further suitable pharmaceutically acceptable in vivo hydrolysable ester group is that of the formula:

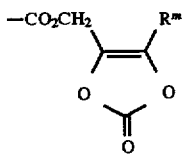

wherein $R^m$ is hydrogen, $(C_{1-6})$ alkyl or phenyl.

A preferred in vivo hydrolysable ester group is the pivaloyloxymethyl ester.

Suitable pharmaceutically acceptable salts of the carboxy group of the compound of formula a) include metal salts, eg aluminium, alkali metal salts such as sodium or potassium, especially sodium, alkaline earth metal salts such as calcium or magnesium, and ammonium or substituted ammonium salts, for example those with lower alkylamines such as triethylamine, hydroxy-lower alkylamines such as 2-hydroxyethylamine, bis-(2-hydroxyethyl)amine or tris-(2-hydroxyethyl)-amine, cycloalkylamines such as dicyclohexylamine, or with procaine, dibenzylamine, N,N-dibenzylethylene-diamine, 1-ephenamine, N-methylmorpholine, N-ethylpiperidine, N-benzyl-β-phenethylamine, dehydroabietylamine, N,N'-bisdehydroabietylamine, ethylenediamine, or bases of the pyridine type such as pyridine, collidine or quinoline, or other amines which have been used to form salts with known penicillins and cephalosporins. Other useful salts include the lithium salt and silver salt. Salts of formula (I) may be prepared by salt exchange in conventional manner.

In compounds of formula (I) or (Ia), the group Y may be an oxidised sulphur atom, i.e. a sulphoxide (SO) or sulphone $(SO_2)$ group. When Y is a Sulphoxide group it will be understood that α- and β-isomers may exist; both such isomers are encompassed within the scope of the present invention.

Preferably Y is O or S, in particular O.

Advantageously, $R^1$ is hydrogen.

Suitably, the cyclic ether or thio-ether at the 3-position of the cephalosporin nucleus is unsubstituted or substituted by up to three substituents $R^4$, selected from $(C_{1-6})$ alkyl, for example methyl, $(C_{1-6})$ alkoxy, for example methoxy, $(C_{1-6})$ alkoxycarbonyl for example methoxycarbonyl, $(C_{1-6})$ alkoxy $(C_{1-6})$ alkyl, for example methoxymethyl, and $(C_{1-6})$ alkanoyloxy $(C_{1-6})$ alkyl, for example acetoxymethyl. Preferably the cyclic ether or thio-ether at the 3-position of the cephalosporin nucleus is unsubstituted.

Preferably m is 1.

Suitably the cyclic ether at the 3-position of the cephalosporin nucleus is a tetrahydrofuran-2-yl group.

Preferably the cyclic thio-ether is bonded to the cephalosporin nucleus at a ring carbon adjacent to the oxygen or sulphur heteroatom.

Suitable acyl groups $R^2$ include those of formulae (a)–(f):

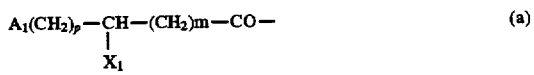  (a)

  (b)

  (c)

  (d)

-continued

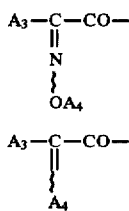

wherein p is 0, 1 or 2; m is 0, 1 or 2; $A_1$ is $(C_{1-6})$ alkyl, substituted $(C_{1-6})$ alkyl wherein the substituents may be as for $R^4$ above, $(C_{3-6})$ cycloalkyl, cyclohexenyl, cyclohexadienyl, an aryl (including heteroaryl) group, such as phenyl, substituted phenyl, thienyl, pyridyl, or an optionally substituted thiazolyl group, a $(C_{1-6})$ akylthio group or $(C_{1-6})$ alkyloxy; $X_1$ is a hydrogen or halogen atom, a carboxylic acid, carboxylic ester, sulphonic acid, azido, tetrazolyl, hydroxy, acyloxy, amino, ureido, acylamino, heterocyclylamino, guanidino or acylureido group; $A_2$ is an aryl group, for example a phenyl, 2,6-dimethoxyphenyl, 2-alkoxy-1-naphthyl, 3-arylisoxazolyl, or a 3-aryl-5-methylisoxazolyl group, such as 3-(2-chloro-6-fluorophenyl)-5-methylisoxazol-4-yl; a substituted alkyl group; or a substituted dithietane; $X_2$ is a —$CH_2OCH_2$—, —$CH_2SCH_2$— or alkylene group; $X_3$ is an oxygen or sulphur atom; $A_3$ is an aryl or heteroaryl group such as phenyl, substituted phenyl, furyl, aminothiazolyl or aminothiadiazolyl in which the amino group is optionally protected; and $A_4$ is hydrogen, $(C_{1-6})$alkyl, $(C_{3-8})$ cycloalkyl, $(C_{3-8})$ cycloalkyl$(C_{1-6})$alkyl, $(C_{1-6})$ alkoxycarbonyl$(C_{1-6})$ alkyl, $(C_{2-6})$ alkenyl, carboxy$(C_{1-6})$alkyl, $(C_{2-6})$ alkynyl, aryl or $(C_{1-6})$alkyl substituted by up to three aryl groups.

Suitably when $R^2$ is a group (a), $A_1$ is $(C_{1-6})$ alkyl, $(C_{3-6})$ cycloalkyl, cyclohexenyl, cyclohexadienyl, phenyl, substituted phenyl (eg substituted as for "aryl" above) such as hydroxyphenyl, thienyl or pyridyl; and $X_1$ is a hydrogen or halogen atom, or a carboxy, carboxylic ester, azido, tetrazolyl, hydroxy, acyloxy, optionally protected amino, ureido, guanidino or acylureido group.

Suitably when $R^2$ is a group of formula (d), $A_2$ is phenyl, $X_3$ is oxygen and p is O.

Alternatively when $R^2$ is a group of formula (e) or (f) suitable values for the group $A_3$ include those commonly found in antibacterially active cephalosporins containing a hydroxyimino, substituted hydroxyimino or vinyl group in the side chain attached to position 7 of the cephalosporin nucleus, for example phenyl, thien-2-yl, thien-3-yl, fur-2-yl, fur-3-yl, pyrid-2-yl, pyrid-3-yl, pyrid-4-yl, 5-amino-1,2,4-thiadiazol-3-yl and 2-aminothiazol-4-yl in each of which the amino group is optionally protected.

Preferred groups for $A_3$ include phenyl, 2-aminothiazol-4-yl, fur-2-yl, thien-2-yl, 2-(2-chloroacetamido)thiazol-4-yl, 2-tritylamino-thiazol-4-yl, 5-amino-1,2,4-thiadiazol-3-yl and 4-aminopyrimid-2-yl.

In compounds of formula (Ia) a preferred acyl group $R^2$ is one of formula (e), having a group, $A_3$ which is 2-aminothiazol-4-yl.

Suitable values for the group $A_4$ include hydrogen, methyl, ethyl, cyclopropylmethyl, triphenylmethyl (trityl), cyclobutyl, cyclopentyl, cyclohexyl, cycloheptyl, cyclooctyl, phenyl, carboxymethyl, carboxypropyl and t-butoxycarbonylmethyl.

Preferred values for $A_4$ in compounds of formula (Ia) include methyl and hydrogen.

It will be appreciated that compounds of the invention wherein $R^2$ is a group of formula (e) or (f) can exist as syn and anti (or E and Z) isomers or mixtures thereof. Both isomers are encompassed within the scope of this invention.

Preferably the compounds of the invention wherein $R^2$ is a group of formula (e) have the syn configuration (i.e. have the group $OA_4$ syn to the amide linkage) or are enriched in that isomer.

Similarly, when $R^2$ is a group of formula (f), the group $A_4$ is preferably cis to the amide linkage, i.e. when group (f) is 2-amino-thiazol-4-yl, the Z-configuration is preferred.

Preferably in formula (I) and (Ia) if the 3-position substituent is a tetrahydrofuran-2-yl ring system the compound has the configuration:

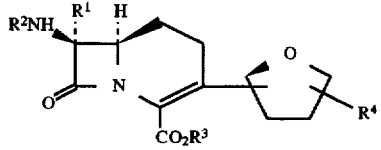

Certain compounds of the invention include an amino group which may be protected. Suitable amino protecting groups are those well known in the an which may be removed under conventional conditions without disruption of the remainder of the molecule.

Examples of amino protecting groups include $(C_{1-6})$ alkanoyl; benzoyl; benzyl optionally substituted in the phenyl ring by one or two substituents selected from $(C_{1-4})$ alkyl, $(C_{1-4})$ alkoxy, trifluoromethyl, halogen, or nitro; $(C_{1-4})$ alkoxycarbonyl; benzyloxycarbonyl or trityl (ie triphenylmethyl) substituted as for benzyl above; allyloxycarbonyl, trichloroethoxycarbonyl or chloroacetyl.

When used herein the term 'aryl' includes phenyl and naphthyl, each optionally substituted with up to five, preferably up to three, groups selected from halogen, mercapto, $(C_{1-6})$ alkyl, phenyl, $(C_{1-6})$ alkoxy, hydroxy$(C_{1-6})$alkyl, mercapto$(C_{1-6})$alkyl, halo$(C_{1-6})$ alkyl, hydroxy, amino, nitro, carboxy, $(C_{1-6})$alkylcarbonyloxy, $(C_{1-6})$ alkoxycarbonyl, formyl, or $(C_{1-6})$alkylcarbonyl groups.

The terms 'heterocyclyl' and 'heterocyclic' as used herein include aromatic and non-aromatic, single and fused, rings suitably containing up to four hetero-atoms in each ring selected from oxygen, nitrogen and sulphur, which rings may be unsubstituted or substituted by, for example, up to three groups selected from halogen, $(C_{1-6})$alkyl, $(C_{1-6})$ alkoxy, halo$(C_{1-6})$alkyl, hydroxy, carboxy, carboxy salts, carboxy esters such as $(C_{1-6})$alkoxycarbonyl, $(C_{1-6})$ alkoxycarbonyl$(C_{1-6})$alkyl, aryl, and oxo groups. Each heterocyclic ring suitably has from 4 to 7, preferably 5 or 6, ring atoms. The term 'heteroaryl' refers to heteroaromatic, heterocyclic rings. A fused heterocyclic ring system may include carbocyclic rings and need include only one heterocyclic ring. Compounds within the invention containing a heterocyclyl group may occur in two or more tautometric forms depending on the nature of the heterocyclyl group; all such tautomeric forms are included within the scope of the invention.

The term 'heteroaryl' as used herein means a heteroaromatic heterocyclic ring or ring system, suitably having 5 or 6 ring atoms in each ring.

When used herein the terms 'alkyl', 'alkenyl', 'alkynyl' and 'alkoxy' include straight and branched chain groups containing from 1 to 6 carbon atoms, such as methyl, ethyl, propyl and butyl. A particular alkyl group is methyl.

When used herein the term 'halogen' refers to fluorine, chlorine, bromine and iodine.

Some of the compounds of this invention may be crystallised or recrystallised from solvents such as organic solvents. In such cases solvates may be formed. This invention includes within its scope stoichiometric solvates including hydrates as well as compounds containing variable amounts of water that may be produced by processes such as lyophilisation.

Since the antibiotic compounds of the invention are intended for use in pharmaceutical compositions it will readily be understood that they are each provided in substantially pure form, for example at least 60% pure, more suitably at least 75% pure and preferably at least 85%, especially at least 95% pure, particularly at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 49% of a compound of the formula (I) or salt thereof.

Specific compounds within this invention of formula (Ia) include the following pharmaceutically acceptable carboxylic acids, salts and in-vivo hydrolysable esters:

Pivaloyloxymethyl (6R,7S)-7-[2-(2-aminothiazol-4-yl)-2-(Z)-methoxyiminoacetamido]-[(S)-tetrahydrofuran-2-yl]-1-carba-1-dethiaceph-3-em4-carboxylate, Sodium (6R,7S)-7-[2-(2-aminothiazol-4-yl)-2-(Z)-methoxyiminoacetamido]-3-[(S)-tetrahydrofuran-2-yl]-1-carba-1-dethiaceph-3-em-4-carboxylate, 4-Methoxybenzyl (6R,7S)-7-phenylacetamido-3-[(R and S)-tetrahydrofuran-2-yl]-1-carb-1-dethiaceph-3-em4-carboxylate, 4-Methoxybenzyl (6R,7S)-7-phthalimido-3-[(S)-tetrahydrofuran-2-yl]-1-carba-1-dethiaceph-3-em-4-carboxylate, Sodium (6R,7S)-7-[2-(2-aminothiazol-4-yl)-2-(Z)-prop-2-yloxyiminoacetamido]-3-[(2S)-tetrahydrofuran-2-yl]-1-carba-1-dethiaceph-3-em-4-carboxylate, 4-Methoxybenzyl (6R,7S)-7-[2-(2-aminothiazol-4-yl)-2-(Z)-prop-2-yloxyiminoacetamido]-3-[(2S)-tetrahydrofuran-2-yl]-1-carba-1-dethiaceph-3-em-4-carboxylate, Sodium (6R,7S)-7-[2-(2-aminothiazol-4-yl)-2-(Z)-hydroxyiminoacetamido]-3-[(2S)-tetrahydrofuran-2-yl]-1-carba-1-dethiaceph-3-em-4-carboxylate, 4-Methoxybenzyl (6R,7S)-7-[2-(2-aminothiazol-4-yl)-2-(Z)-hydroxyiminoacetamido]-3-[(2S)-tetrahydrofuran-2-yl]-1-carba-1-dethiaceph-3-em-4-carboxylate, Sodium (6R,7S)-7-[2-(2-aminothiazol-4-yl)-2-(Z)-difluoromethoxyiminoacetamido]-3-[(2S)-tetrahydrofuran-2-yl]-1-carba-1-dethiaceph-3-em-4-carboxylate, The present invention provides a process for the preparation of a compound of formula (I) or (Ia) as defined above in which $-CO_2R^3$ is a carboxy group or carboxylate anion or $R^3$ is a pharmaceutically acceptable salt-forming group or in vivo hydrolysable ester group, wherein a compound of formula (I) as defined above in which $R^3$ is a carboxy protecting group has its group $CO_2R^3$ replaced by a group $CO_2R^3$ which is a carboxy group or a carboxylate anion, or in which $R^3$ is a pharmaceutically acceptable salt-forming group or in-vivo hydrolysable ester group.

The present invention further provides a process for the preparation of a compound of formula (I), which process comprises treating a compound of formula (II) or a salt thereof:

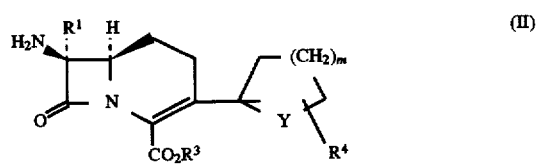

wherein $R^1$, $CO_2R^3$, $R^4$, m, and Y are as hereinbefore defined, wherein any reactive groups may be protected, and wherein the amino group is optionally substituted with a group which permits acylation to take place; with an acid of formula (III) or a N-acylating derivative thereof:

$$R^2OH \qquad (III)$$

wherein $R^2$ is the acyl group as defined with respect to formula (I) and wherein any reactive groups may be protected; and thereafter, if necessary or desired, carrying out one or more of the following steps:

i) removing any protecting groups;
ii) converting the group $CO_2R^3$ into a different group $CO_2R^3$;
iii) converting the group $R^2$ into a different group $R^2$;
iv) converting the group Y into a different group Y, for example S into SO or $SO_2$;
v) converting the product into a salt or ester.

Acids of formula (III) may be prepared by methods known in the art, or methods analogous to such processes. Suitable processes include those described, for example, in UK Patent 2 107 307 B, UK Patent Specification No. 1,536,281, and U.K. Patent Specification No. 1,508,064.

Suitable groups which permit acylation to take place and which are optionally present on the amino group of the stating material of the formula (II) include N-silyl, N-stannyl and N-phosphorus groups, for example trialkylsilyl groups such as trimethylsilyl, trialkyltin groups such as tri-n-butyltin, groups of formula $-P.R^7R^8$ wherein $R^7$ is an alkyl, haloalkyl, aryl, aralkyl, alkoxy, haloalkyl, aryl, aralkyl, alkoxy, haloalkoxy, aryloxy, aralkyloxy or dialkylamino group, $R^8$ is the same as $R^7$ or is halogen or $R^7$ and $R^8$ together form a ring; suitable such phosphorus groups being $-P(OC_2H_5)_2$, $-P(C_2H_5)_2$,

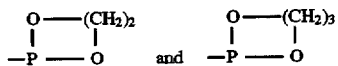

A group which may optionally be introduced onto the amino group in the compound of formula (II) is trimethylsilyl.

Advantageously the silylation reaction may be carried out in situ, prior to the acylation reaction, with a silylating agent that does not require concomitant addition of base. Suitable silylating agents include, for example, N-(trimethylsilyl)-acetamide, N,O-bis-(trimethylsilyl)acetamide, N,O-bis (trimethylsilyl)-trifluoroacetamide, N-methyl-N-trimethylsilylacetamide, N-methyl-N-trimethylsilyl-trifluoroacetamide, N,N'-bis(trimethylsilyl)urea, and N,O-bis(trimethylsilyl)carbamate. A preferred silylating agent is N,O-bis(trimethylsilyl)acetamide. The silylation reaction may suitably be carried out in an inert, anhydrous organic solvent such as dichloromethane at room temperature or at an elevated temperature, for example 30°–60° C., preferably 40°–50° C.

The above process may optionally be carried out in the presence of a small quantity, for example 0.1 equivalents, of a silyl halide, for example a tri($C_{1-6}$)alkylsilyl halide, especially trimethylsilyl chloride.

A reactive N-acylating derivative of the acid (III) is employed in the above process. The choice of reactive derivative will of course be influenced by the chemical nature of the substituents of the acid.

Suitable N-acylating derivatives include an acid halide, preferably the acid chloride or bromide or alternatively a symmetrical or mixed anhydride. The acylation may be effected in the presence of an acid binding agent for example, tertiary amine (such as pyridine or dimethylaniline), molecular sieves, an inorganic base (such as calcium carbonate or sodium bicarbonate) or an oxirane, which binds hydrogen halide liberated in the acylation reaction. The oxirane is preferably a $(C_{1-6})$-1,2-alkylene oxide—such as ethylene oxide or propylene oxide. The acylation reaction using an acid halide may be carried out at a temperature in the range −50° C. to +50° C., preferably −20° C. to +20° C., in aqueous or non-aqueous media such as water, acetone, tetrahydrofuran, ethyl acetate, dimethylacetamide, dimethylformamide, acetonitrile, dichloromethane, 1,2-dichloroethane, or mixtures thereof. Alternatively, the reaction may be earned out in an unstable emulsion of water-immiscible solvent, especially art aliphatic ester or ketone, such as methyl isobutyl ketone or butyl acetate. The acylation with acid halide or anhydride is suitably carried out in the presence of a basic catalyst such as pyridine or 2,6-lutidine.

Acid halides may be prepared by reacting the acid (III) or a salt or a reactive derivative thereof with a halogenating (eg chlorinating or brominating) agent such as phosphorus pentachloride, thionyl chloride, oxalyl chloride or phosgene.

Suitable mixed anhydrides are anhydrides with, for example, carbonic acid monoesters, trimethyl acetic acid, thioacetic acid, diphenylacetic acid, benzoic acid, phosphorus acids (such as phosphoric, phosphorous, and phosphinic acids) or aromatic or aliphatic sulphonic acids (such as p-toluenesulphonic acid or methanesulphonic acid).

Alternative N-acylating derivatives of acid (III) are the acid azide, or activated esters such as esters with 2-mercaptopyridine, cyanomethanol, p-nitrophenol, 2,4-dinitrophenol, thiophenol, halophenols, including pentachlorophenol, monomethoxyphenol, N-hydroxy succinimide, N-hydroxybenzotriazole, or 8-hydroxyquinoline; or amides such as N-acylsaccharins, N-acylthiazolidin-2-thione or N-acylphthalimides; or an alkylidene iminoester prepared by reaction of the acid (III) with an oxime.

Other reactive N-acylating derivatives of the acid (III) include the reactive intermediates formed by reaction in situ with a condensing agent such as a carbodiimide, for example, N,N'-diethyl-, dipropyl-or diisopropylcarbodiimide, N,N'-di-cyclohexyl-carbodiimide, or N-ethyl-N'-[3-(dimethylamino)propyl]carbodiimide; a suitable carbonyl compound, for example, N,N'-carbonyldiimidazole or N,N'-carbonyldi-triazole; an isoxazolinium salt, for example, N-ethyl-5-phenylisoxazolinium-3-sulphonate or N-t-butyl-5-methylisoxazolinium perchlorate; or an N-alkoxycarbonyl 2-alkoxy-1,2-dihydroquinoline, such as N-ethoxycarbonyl 2-ethoxy-1,2-dihydroquinoline. Other condensing agents include Lewis acids (for example $BBr_3$—$C_6H_6$); or a phosphoric acid condensing agent such as diethylphosphorylcyanide. The condensation reaction is preferably carried out in an organic reaction medium, for example, methylene chloride, dimethylformamide, acetonitrile, alcohol, benzene, dioxan or tetrahydrofuran.

A further method of forming the N-acylating derivative of the acid of formula (III) is to treat the acid of formula (III) with a solution or suspension preformed by addition of a carbonyl halide, preferably oxalyl chloride, or a phosphoryl halide such as phosphorus oxychloride, to a halogenated hydrocarbon solvent, preferably dichloromethane, containing a lower acyl tertiary amide, preferably N,N-dimethylformamide. The N-acylating derivative of the acid of formula (III) so derived may then be caused to react with a compound of formula (II). The acylation reaction may conveniently be carried out at −40° to +30° C., if desired in the presence of an acid binding agent such as pyridine. A catalyst such as 4-dimethylaminopyridine may optionally also be added. A preferred solvent for the above acylation reaction is dichloromethane.

The optional removal of protecting group (i), the optional conversion of $CO_2R^3$ (ii), the optional conversion (iii) of $R^2$ to a different $R^2$, $CO_2R^3$ to a different $CO_2R^3$ and (iv), Y to a different Y, and (v) the optional formation of a salt or ester, may be carried out using methods well known in the art of cephalosporin and penicillin chemistry.

For example, when the group Y is S, SO, or $SO_2$, the group Y may be converted into a different group Y by methods of oxidation or reduction well known in the art of cephalosporin and penicillin synthesis, as described, for example, in European Patent Application Publication No. 0 114 752. For example, sulphoxides (in which Y is SO) may be prepared from the corresponding sulphide (in which Y is S) by oxidation with a suitable oxidising agent, for example an organic peracid such as m-chloroperbenzoic acid.

A reduction step is generally effected by processes well known in the art of β-lactam chemistry; for example using phosphorus trichloride in dimethylformamide.

For example, removal of protecting groups may be earned out by any convenient method known in the art such that unwanted side reactions are minimised. When for example $R^3$ is the protecting group p-methoxybenzyl, this group may suitably be removed by treatment of the protected compound with aluminium chloride in the presence of anisole. Separation of unwanted by-products may be carried out using standard methods.

Compounds of formula (I), (Ia) and (II) may be made by further processes of this invention.

For example in one further process "route A" a compound of formula (II) may be formed by cyclising a compound of formula (IV):

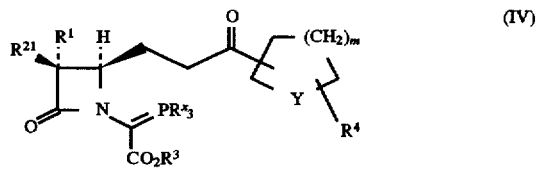

where $R^1$, $R^3$, $R^4$, and m are as defined in formula (I), $R^{21}$ is a group $R^2NH$ or a group which can be converted into $R^2NH$ and $R^x$ is alkyl.

Suitably $R^{21}$ may be a substituted or protected amino group such as phenylacetamido, from which the substituting or protecting group may be removed in a deprotection step. In the case of phenylacetamido this deprotection may be carried out using the known Delft cleavage reaction. Suitable reaction conditions for Delft cleavage include treatment with phosphorus pentachloride and N-methylmorpholine at reduced temperature. Alternatively $R^{21}$ may be a group which may be converted into or replaced by an amino group, for example a phthalimido group, which may replaced by an amino group by treatment with a hydrazine such as methyl hydrazine.

Suitably R* may be n-butyl.

Suitably the cyclisation reaction may be carried out by refluxing in an organic solvent such as toluene in the presence of benzoic acid.

Compounds of formula (IV) may for example be prepared from compounds of formula (V):

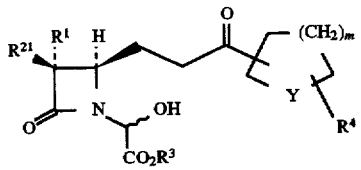
(V)

where $R^1$, $R^{21}$, $R^3$, $R^4$ and m are as defined above, by for example replacement of the hydroxy group shown with a halogen, preferably chlorine, using for example a halogenating agent such as thionyl chloride in the presence of a base such as lutidine, followed by reaction of the chloro compound with $PR^x{}_3$.

Compounds of formula (V) may for example be prepared from compounds of formula (VI):

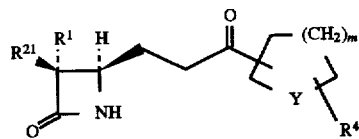
(VI)

where $R^1$, $R^{21}$, $R^4$ and m are or defined above, by for example reaction with the appropriate $R^3$-glyoxylate, for example p-methoxybenzyl glyoxylate, for example at 0° C. in the presence of a base such as methylamine.

Compounds of formula (VI) may for example be prepared from compounds of formula (VII)

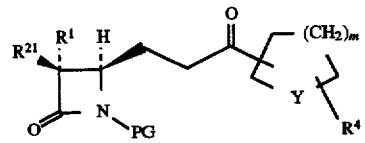
(VII)

where $R^1$, $R^{21}$, $R^4$ and m are as defined above, where PG is an amino protecting group such as p-methoxyphenyl, by removal of this protecting group, eg in the case of p-methoxyphenyl using aqueous ceric ammonium nitrate.

Compounds of formula (VII) may for example be prepared from compounds of formula (VIII):

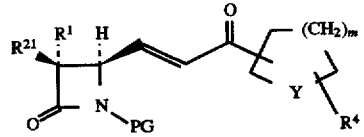
(VIII)

where $R^1$, $R^{21}$, $R^4$, m and PG are as defined above, by for example hydrogenation of the alkene using Pd/C and hydrogen.

Compounds of formula (VIII) may for example be prepared from compounds of formula (IX):

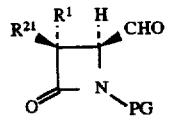
(IX)

where $R^1$, $R^{21}$ and PG are as defined above by reaction with a compound of formula (X)

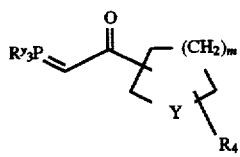
(IX)

where $R^Y$ is an organic group such as phenyl, Y, m and $R^4$ are as defined above, for example by stirring together in a solvent at room temperature.

Compounds of formula (X) may be prepared from known (see WO 92/01696) compounds of formula (X):

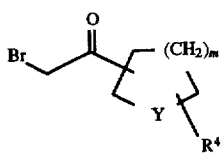
(XI)

where Y, $R^4$ are m are as defined above by reaction with a compound $R^y{}_3P$ where Ry is an organic group such as phenyl.

Compounds of formula (IX) may for example be prepared from compounds of formula (XII):

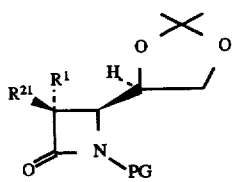
(XII)

where $R^1$, $R^{21}$ and PG are as defined above by reaction with periodic acid in a suitable solvent such as a tetrahydrofuran/water mixture.

Compounds of formula (XII) may for example be prepared from compounds of formula (XIII):

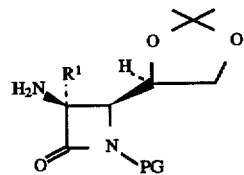
(XIII)

where $R^1$ and PG are as defined above, by reaction with an acid of formula $R^{21}$ COOH or an acylating derivative thereof such as an acyl chloride, for example phenylacetyl chloride.

Compounds of formula (XIII) may for example be prepared from the known compound L-(S)-glyceraldehyde acetonide (XVI):

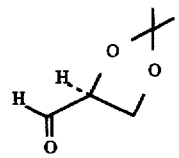
(XVI)

which may be prepared as described in C. Hubschwerlen "Synthesis" (1986), (962), by treatment of (XVI) with p-anisidine for example in a solvent such as dichloromethane to form a compound of formula (XV):

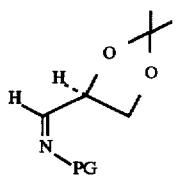

where PG is a protecting group as defined above. The compound of formula (XV) may then be cyclised to form the acetidinone (XIV):

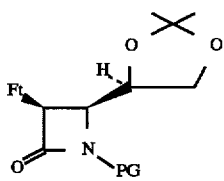

where Ft represents phthlalimido, by reaction of the compound of formula (XV) with phthalimidoacetyl chloride. The phthalimido group Ft may be removed and replaced by an amino group in a compound of formula (XIII) by treatment of the compound (XIV) with methylhydrazine.

For example in a second further process "route B", a compound of formula (II) in the form of a mixture of diastereoisomers, which may be resolved, may be for example prepared from a compound of formula (XVII):

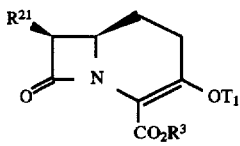

where $R^{21}$ and $R^3$ are as defined above and Tf represents trifluoromethanesulphonyloxy, by reaction with a compound of formula (XVIII):

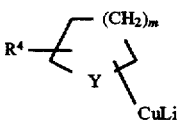

where Y, $R^4$ and m are as defined above. Compounds of formula (XVIII) may be prepared for example from known (J. Amer. Chem. Soc. (1988) 110 842) compounds of formula (XIX)

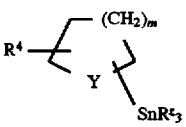

where $R^4$, Y and m are as defined above, and $R^z$ is alkyl, by reaction with n-butyl lithium then with a copper (I) bromide dimethylsulphide complex.

Compounds of formula (XVII) may for example be prepared from compounds of formula (XX):

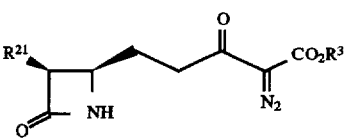

where $R^{21}$ and $R^3$ are as defined above, by reflux with a rhodium (II) catalyst, followed by cooling and sequential treatment with a base such as N,N-diisopropylethylamine then trifluoromethanesulfonic anhydride.

Compounds of formula (XX) may be prepared from compounds of formula (XXI):

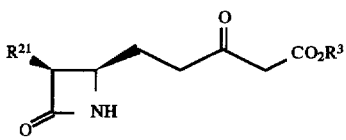

where $R^{21}$ and $R^3$ are as defined above, by reaction of the compound (XXI) with azide, such as 4-toluenesulphonyl azide in the presence of a base such as N,N-diisopropylethylamine.

Compounds of formula (XXI) may be prepared from compounds of formula (XXII):

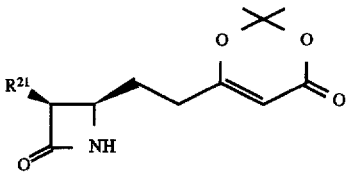

by reaction of the compound (XXII) with an alcohol $R^3OH$, such as p-methoxybenzyl alcohol, for example under reflux.

Compounds of formula (XXII) may for example be prepared by hydrogenation, eg using Pd/C and hydrogen, of compounds of formula (XXIII):

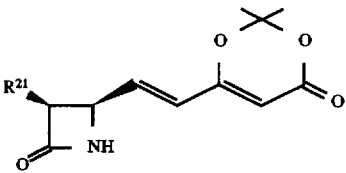

where $R^{21}$ is as defined above and the amino group in the azetidinone ring may optionally be protected by a protecting group PG as described above, which may be removed as described above to yield the compound of formula (XXII).

Compounds of formula (XXIII) may be prepared from compounds of formula (IX) described above with reference to route A, by reaction with known (Oppi Briefs (1990), 22:1, p109–111, C. Bodurow et al) 2,2-(dimethyl)-6-[(triphenylphosphoranylidene)methyl]-4H-1,3-dioxin-4-one:

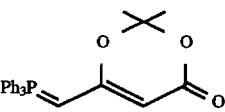

Compounds of formula (II), (IV), (V), (VI), (VII), (VIII), (XII), (XIII), (XX), (XXI), (XXII) and (XXIII) are novel compounds and as such form part of the invention.

The present invention also provides a pharmaceutical composition which comprises a compound of formula (I) or a pharmaceutically acceptable salt or in vivo hydrolysable ester thereof and a pharmaceutically acceptable carrier. The compositions of the invention include those in a form adapted for oral, topical or parenteral use and may be used for the treatment of bacterial infection in mammals including humans.

The antibiotic compounds according to the invention may be formulated for administration in any convenient way for use in human or veterinary medicine, by analogy with other antibiotics.

The composition may be formulated for administration by any route, such as oral, topical or parenteral, especially oral. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

No unacceptable toxicological effects are expected when a compound of formula (Ia) or a pharmaceutically acceptable salt or in vivo hydrolysable ester thereof is administered in the above-mentioned dosage range.

The compound of formula (Ia) may be the sole therapeutic agent in the compositions of the invention or a combination with other antibiotics or with a β-lactamase inhibitor may be employed.

Advantageously, the compositions also comprise a compound of formula (XIII) or a pharmaceutically acceptable salt or ester thereof:

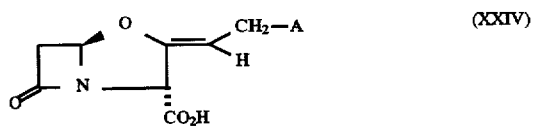

(XXIV)

wherein

A is hydroxyl, substituted hydroxyl, thiol, substituted thiol, amino, mono- or di-hydrocarbyl-substituted amino, or mono-or di-acylamino; an optionally substituted triazolyl group; or an optionally substituted tetrazolyl group as described in EP-A-0 053 893.

A further advantageous composition comprises a compound of formula (Ia) or a pharmaceutically acceptable salt or in vivo hydrolysable ester thereof together with a compound of formula (XXV) or a pharmaceutically acceptable salt or in vivo hydrolysable ester thereof:

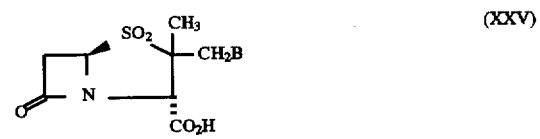

(XXV)

wherein

B represents hydrogen, halogen or a group of formula:

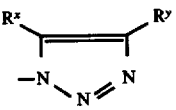

in which $R^x$ and $R^y$ are the same or different and each represents hydrogen, $(C_{1-6})$ alkoxycarbonyl or carboxy, or a pharmaceutically acceptable salt thereof.

Further suitable β-lactamase inhibitors include 6-alkylidene penems of formula (XXVI):

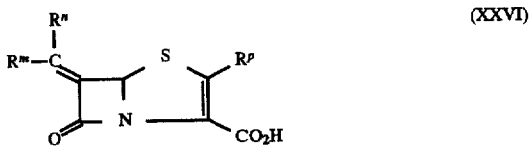

(XXVI)

or a pharmaceutically acceptable salt or in vivo hydrolysable ester thereof, wherein $R'''$ and $R''$ are the same or different and each represents hydrogen, or a $(C_{1-10})$ hydrocarbon or heterocyclic group optionally substituted with a functional group; and RP represents hydrogen or a group of formula $R^r$ or —$SR^r$ where $R^r$ is an optionally substituted ($C_{1-10}$) hydrocarbon or heterocyclic group, as described in EP-A-0 041 768.

Further suitable β-lactamase inhibitors include 6β-bromopenicillanic acid and pharmaceutically acceptable salts and in vivo hydrolysable esters thereof and 6β-iodopenicillanic acid and pharmaceutically acceptable salts and in vivo hydrolysable esters thereof described in, for example, EP-A-0 410 768 and EP-A-0 154 132 (both Beecham Group).

Such compositions of this invention which include a β-lactamase inhibitory amount of a β-lactamase inhibitor are formulated in a conventional manner using techniques and procedures per se known in the art.

The antibiotic compounds of the present invention are active against a wide range of organisms including both Gram-negative organisms such as *E. coli* and Gram-positive organisms such as *S. aureus*.

The following Examples illustrate the preparation of compounds of the invention and intermediates thereto.

EXAMPLE 1 (Route A)

Pivaloyloxymethyl (6R,7S)-7-[2-(2-aminothiazol-4-yl)-2-(Z)-methoxyiminoacetamido]-[(S)-tetrahydrofuran-2-yl]-1-carba-1-dethiaceph-3-em-4-carboxylate a) (3S,4S)-4-[(R)-2,2-Dimethyl-1,3-dioxolon-4-yl]-1-(4-methoxyphenyl)-3-phthalimidoazetidin-2-one A crude aqueous solution of L-(S)-glyceraldehyde acetonide (obtained from 0.15 mol of 5,6-isopropylidene-L-gulono-1,4-lactone, C. Hubschwerlen, Synthesis, 1986, 962) was treated with a solution of p-anisidine (16.2 g., 0.13 mol) in dichloromethane (300 ml). The reaction mixture was stirred overnight at room temperature, then the organic phase separated and the aqueous phase extracted twice with dichloromethane (100 ml). The combined organic layers were dried over magnesium sulphate, filtered and reduced in volume to ~200 ml. The crude imine was treated with triethylamine (26.7 ml, 0.19 mol) and cooled to −30° C. A solution of phthalimidoacetyl chloride (42.8 g, 0.19 mol) in dichloromethane (150 ml) was added dropwise over 45 min. After stirring for 2.5 h at room temperature, the reaction mixture was filtered, and the filtrate washed successively with water (×3), 1M hydrochloric acid, saturated aqueous sodium hydrogen carbonate solution, water and brine. The organic phase was dried over magnesium sulphate, filtered and concentrated in vacuo. The residue was passed through a short column of silica eluting with dichloromethane, concentrated, and the residue purified by crystallisation from ethyl acetate/hexane. The title compound as obtained as a yellow solid (23.78 g, 44%); m.p. 164°–166° C.; [α]$_D$+55.0° (c 1.00 CHCl$_3$); (Found: C, 65.44; H, 5.27; N, 6.75%; $M^+$422.1487. $C_{23}H_{22}N_2O_6$ requires C, 65.40; H, 5.25; N, 6.63%; M 422.1478.); $v_{max}$ (CH$_2$Cl$_2$) 1760, 1724, 1514, 1384, 1265 and 1247 cm$^{-1}$; δ$_H$ (CDCl$_3$) 1.27 (3H, s), 1.50 (3H, s), 3.53 (1H, dd, J 8.4, 6.5 Hz), 3.75 (1H, dd, J 8.4, 6.5 Hz), 3.82 (3H, s), 4.42–4.57 (2H,m), 5.53 (1H, d, J 5.4 Hz), 6.91 (2H, d, J 9.1 Hz), 7.74 (2H, d, J 9.1 Hz), 7.70–7.84 (2H, m) and 7.89–7.95 (2H, m).

b) (3S,4S)-3 Amino-4-[(R)-2,2-dimethyl-1,3-dioxolon-4-yl]-1-(4-methoxyphenyl)azetidin-2-one Methyl hydrazine (8.1 ml, 152.3 mmol) was added to a solution of (3S,4S)-4-[(R)-2,2-dimethyl-1,3-dioxolan-4-yl]-1-(4-methoxyphenyl)-3-phthalimidoazetidin-2-one (23.78 g, 56.4 mmol) in dichloromethane (230 ml). The reaction mixture was heated at reflux for 6 h and then stirred overnight at room temperature. The precipitated solid was filtered off through celite and the filtrate washed successively with saturated aqueous sodium hydrogen carbonate solution and brine. After drying over magnesium sulphate, the solvent was evaporated in vacuo to yield a pale yellow solid. Recrystallisation from dichloromethane/hexane yielded the title compound as a white solid (12.26 g, 74%); m.p. 163°–165° C.; [α]$_D$−98.5° (c 1.00 MeOH); (Found: $M^+$292.1428. $C_{15}H_{20}N_2O_4$ requires M 292.1423); $v_{max}$ (CH$_2$Cl$_2$) 1744, 1513 and 1270 cm$^{-1}$; δ$_H$ (CDCl$_3$) 1.35 (3H, s), 1.43 (3H, s), 1.70 (2H, br.s, exch.), 3.79 (3H, s), 3.85 (1H, m), 4.20 (1H, m), 4.27–4.38 (3H, m), 6.86 (2H, d, J 9.0 Hz) and 7.55 (2H, d, J 9.0 Hz).

c) (3S,4S)-4-[(R)-2,2-Dimethyl-1,3-dioxolan-4-yl]-1-(4-methoxyphenyl)-3-phenylacetamidoazetidin-2-one A solution of (3S,4S)-3-amino-4-[(R)-2,2-dimethyl-1,3-dioxolan-4-yl]-1-(4-methoxyphenyl)azetidin-2-one (12.21 g, 41.8mmol) in dichloromethane (160 ml) was cooled to 0° C. and treated sequentially with phenylacetyl chloride (6.1 ml, 46.1 mmol), then triethylamine (6.4 ml, 45.9 mmol). After stirring at 0° C. for 15min., the mixture was warmed to room temperature and stirred for a further 30 min. The reaction mixture was diluted with dichloromethane and washed twice with water, then brine. The organic layer was dried over magnesium sulphate, filtered and the solvent evaporated in vacuo to yield a solid. Trituration with diethyl ether yielded the title compound (16.16 g, 94%) as a white amorphous solid; [α]$_D$ 0.0° (c=1.00 DMF); $v_{max}$ (KBr) 1757, 1661 and 1510 cm$^-$; δ$_H$ (CDCl$_3$) 1.16 (3H, s), 1.25 (3H, s), 3.62 (2H, s), 3.69–3.82 (2H, m), 3.76 (3H, s), 4.02 (1H, m), 4.36 (1H, dd, J 5.5, 4.0 Hz), 5.58 (1H, dd, J 9.4, 5.5 Hz), 6.56 (1H, d, J 9.4 Hz), 6.83 (2H, d, J 8.9 Hz) and 7.25–7.40 (7H, m); m/z (EI) 410 (5); (CI, +ve ion, ammonia) 411 (MH$^+$).

d) (3S,4S)-4-Formyl-1-(4-methoxyphenyl)-3-phenylacetamidoazetidin-2-one

Periodic acid (18.7 g, 45.6 mmol) was added to a suspension of (3S,4S)-4-[(R)-2,2-dimethyl-1,3-dioxolan-4-yl]-1-(4-methoxyphenyl)-3-phenylacetamidoazetidin-2-one (15.1 g, 36.8mmol) in tetrahydrofuran (210 ml) and water (210 ml). The reaction mixture was heated under reflux for 1.5 h and then cooled in ice. The precipitated product was collected by filtration, washed with water and dried over phosphorus pentoxide to yield the title compound as a mixture of aldehyde and the corresponding hydrate (10.18 g, 82%); $v_{max}$ (KBr) 1713, 1638, 1552 and 1514 cm$^{-1}$; aldehyde δ$_H$ (d$_6$-DMSO) 3.43 and 3.50 (2H, ABq, J 14.4 Hz), 3.73 (3H, s), 4.95 (1H, dd, J 6.1, 1.2 Hz), 5.19 (1H, m), 6.95 (2H, d, J 9.0 Hz), 7.18–7.35 (7H, m), 9.09 (1H, d, J 7.3 Hz) and 9.52 (1H, d, J 1.2 Hz); hydrate δ$_H$ (d$_6$-DMSO) 3.50 (2H, s), 3.72 (3H, s), 4.16 (1H, t, J 5.6 Hz), 5.07 (1H, q, J 5.8 Hz), 5.29 (1H, dd, J 9.4, 5.6 Hz), 6.28 (2H, t, J 6.7 Hz, exch.), 6.9 (2H, d, J 9.1 Hz), 7.19–7.35 (5H, m), 7.52 (2H, J 9.1 Hz) and 8.52 (1H, d, J 9.4 Hz); m/z (EI) 338 (10); (CI, +ve ion, ammonia) 339 (MH$^+$), 356 (MNH$_4^+$).

e) (S)-Tetrahydrofuran-2-ylcarbonylmethylenetriphenylphosphorane

A solution of triphenylphosphine (13.6 g, 51.9 mmol) in toluene (50 ml) was added to a solution of crude (S)-2-bromoacetyltetrahydrofuran [prepared from (S)-2-tetrahydrofuroic acid (6.0 g, 51.7 mmol)] in toluene (50 ml) over 30 min. The reaction mixture was stirred overnight and the solid collected by filtration and washed with diethyl ether. (S)-Tetrahydrofuran-2-yl) carbonylmethylenetriphenylphosphonium bromide was isolated as an off-white solid (14.5 g, 62% from (S)-2- tetrahydrofuroic acid). The phosphonium salt (14.5 g, 31.9 mmol) was dissolved in water (250 ml) and added dropwise to a solution of sodium carbonate (3.30 g, 31.1 mmol) in water (20 ml). The reaction mixture was stirred for 3 h, after the product collected by filtration and washed with water. After drying over phosphorus pentoxide, the title compound was obtained as a pale yellow solid (10.35 g, 87%); m.p. 169°–172° C.; $[\alpha]_D$–18.3° (c 1.00 CHCl$_{13}$); (Found: C, 77.07; H, 6.15. C$_{24}$H$_{23}$O$_2$P; requires C, 76.99; H, 6.19%); v$_{max}$ (CHCl$_3$) 1523, 1438, 1404, 1108 and 1069 cm$^{-1}$; δ$_H$ (CDCl$_3$) 1.80–2.09 (3H, m), 2.21 (1H, m), 3.89 (1H, m), 4.04 (1H, m), 4.17 (1H, d, J 26.2 Hz), 4.34 (1H, dd, J 7.8, 5.7 Hz) and 7.41–7.70 (15H, m).

f) (3S,4R)-1-(4-Methoxyphenyl)-4-[3-oxo-3-[(S)-tetrahydrofuran-2-yl]propenyl]-3-phenylacetamidoazetidin-2-one A suspension of (3S,4S)-4-formyl-1-(4-methoxyphenyl)-3-phenylacetamidoazetidin- 2-one (10.39 g, 30.7 mmol) in acetonitrile (250 ml) was treated with (S)-tetrahydrofuran-2-ylcarbonylmethylenetriphenylphosphorane (11.50 g, 30.7mmol) and stirred at room temperature for 2 days. The bulk of the product was collected by filtration and washed with acetonitrile. The remainder of the product was purified by chromatography on silica gel eluting with ethyl acetate yielding a further 1.66 g. The title compound was isolated as a white solid (total 12.12 g, 91%); m.p. 159°–162° C.; $[\alpha]_D$–83.4° (c=1 CHCl$_3$); (Found: C, 69.41; H, 6.28; N, 6.20%; M$^+$, 434.1832. C$_{25}$H$_{26}$N$_2$O$_5$ requires: C, 69.11; H, 6.03; N, 6.45%; M 434.11842); vv$_{max}$ (CHCl$_3$) 3414, 1751, 1682, 1631, 1513 and 1250 cm$^{-1}$; δ$_H$ (CDCl$_3$) 1.75–1.92 (3H, m), 2.18 (1H, m), 3.57 (2H, s), 3.76 (3H, s), 3.70–3.90 (2H, m), 4.39 (1H, m), 4.88 (1H, t, J 5.4 Hz), 5.49 (1H, dd, J 8.0, 5.4 Hz), 6.20 (1H, d, J 8.0 Hz), 6.60 (1H, d, J 16.1 Hz), 6.78–6.85 (3H, m) and 7.18–7.38 (7H, m).

g) (3S,4R)-1-(4-Methoxyphenyl)-4-[3-oxo-3-[(S)-tetrahydrofuran-2-yl]propyl]-3-phenylacetamidoazetidin-2-one A solution of (3S,4R)-1-(4-methoxyphenyl)-4-[3-oxo-3-[(S)-tetrahydro-furan-2-yl]propenyl]-3-phenylacetamidoazetidin-2-one (12.1 g, 27.9 mmol) in tetrahydrofuran (250 ml) was hydrogenated over 10% palladium on carbon (1.0 g) for 3h. After filtration through celite, the partially insoluble product was dissolved in dichloromethane and methanol (1: 1) and re-filtered through celite to remove the catalyst. Concentration of the filtrate in vacuo provided the title compound as an amorphous white solid (11.5 g, 95%); (Found: M$^+$436.1997. C$_{25}$H$_{27}$N$_2$O$_5$ requires M436.1998); v$_{max}$ (KBr) 3277, 1758, 1708, 1655, 1542, 1510 and 1246 cm$^{-1}$; δ$_H$ (CDCl$_3$) 1.43 (1H, m), 1.78–1.95 (3H, m), 2.10–2.50 (4H, m), 3.62 (2H, s), 3.75 (3H, s), 3.91 (2H, m), 4.17 (1H, m), 4.24 (1H, m), 5.29 (1H, dd, J 7.8, 5.0 Hz), 6.73 (1H, d, J 7.8 Hz, exch.), 6.81 (2H, d, J 9.0 Hz) and 7.25–7.36 (7H, m).

h) (3S,4R)-4-[3-Oxo-3-[(S)-tetrahydrofuran-2-yl]propyl]-3-phenylacetamidoazetidin-2-one A suspension of (3S,4R)-1-(4-methoxyphenyl)-4-[3-oxo-3-[(S)-tetrahydrofuran-2-yl]-propyl]-3-phenylacetamidoazetidin-2-one (4.66 g, 10.69 mmol) in tetrahydrofuran (200 ml) was treated with a solution of ceric ammonium nitrate (17.3 g, 31.57 mmol) in water (120 ml) at 0° C. After stirring for 30 min. at 0° C., the reaction mixture was diluted with ethyl acetate and the aqueous phase extracted four times with a mixture of tetrahydrofuran and ethyl acetate (2:1). The combined organic extracts were washed successively with 5% aqueous sodium hydrogen carbonate solution, 10% aqueous sodium sulphite solution (×2), 5% aqueous sodium hydrogen carbonate solution, water and then brine. After drying over magnesium sulphate, the solvent was evaporated in vacuo to yield the crude title compound (2.16 g, 61%); (Found: M$^+$330.1586. C$_{18}$H$_{22}$N$_2$O$_4$ requires M 330.1586); v$_{max}$ (CH$_2$Cl$_2$) 3411, 1770, 1715, 1681 and 1512 cm$^{-1}$; δ$_H$ (CDCl$_3$) 1.60–1.96 (5H, m), 2.17 (1H, m), 2.40–2.53 (2H, m), 3.60 (2H, s), 3.78 (1H, m), 3.90 (2H, m), 4.25 (1H, m), 5.22 (1H, dd, J 6.9, 4.9 Hz), 6.39 (1H, br.s, exch.), 6.68 (1H, d, J 9.8 Hz), and 7.25–7.40 (5H, m).

i) 4-Methoxybenzyl (RS)-2-hydroxy-2-[(3S,4R)-4-[3-oxo-3-[(S)-tetrahydrofuran-2-yl]propyl]-3-phenylacetamidoazetidin-2-on-1-yl]acetate p-Methoxybenzyl glyoxylate (3.20 g, 16.5 mmol) in 1,2-dichloroethane (50 ml) was heated at reflux for 1h. using Dean and Stark apparatus. The solution was cooled in ice and treated successively with (3S,4R)-4-[3-oxo-3-[(S)-tetrahydrofuran-2-yl]propyl]-3-phenylacetamidoazetidin-2-one (4.10 g, 12.4 mmol) and triethylamine (170 μl, 1.22 mmol). After stirring at 0° C. for 30 min., the reaction mixture was concentrated in vacuo. The residue was purified by chromatography on silica gel eluting with 50% ethyl acetate in hexane, then ethyl acetate to yield the title compound as a yellow foam (4.53 g, 70%); v$_{max}$ (CH$_2$Cl$_2$) 3420, 3226, 1769, 1743, 1681, 1613 and 1516 cm$^{-1}$; m/z (FAB, +ve ion, 3-nitrobenzyl alcohol/sodium acetate) 547 (MNa$^+$).

j) 4-Methoxybenzyl 2-[(3S,4R)-4-[3-oxo-3-[(S)-tetrahydrofuran-2-yl]propyl]-3-phenylacetamidoazetidin-2-on-1-yl]-2-tri-n-butylphosphoranylidene acetate A solution of thionyl chloride (1.0 ml, 13.71 mmol) in THF (95 ml) was added to the hydroxy compound (4.72 g, 9.01 mmol) and 2,6-lutidine (1.6 ml, 13.74mmol) in THF (50 ml) at –20° C. After stirring for 1 h the reaction mixture was filtered through a pad of celite, and the filtrate evaporated in vacuo. Toluene was added and re-evaporated to yield 4-methoxybenzyl (RS)-2-chloro-2-[(3S,4R)-4-[3-oxo-3-[(S)-tetrahydrofuran-2-yl]propyl]-3-phenylacetamidoazetidin-2-on-1-yl]acetate as an oil.

The crude chloro compound was dissolved in dioxan (30 ml) and treated with tri-n-butylphosphine (4.9 ml, 19.67 mmol). After stirring for 30 min. at room temperature, the reaction mixture was diluted with ethyl acetate and washed successively with dilute sodium hydrogen carbonate solution, water and brine. The organic solution was dried, concentrated and then chromatographed on silica gel eluting with 50, 80% ethyl acetate in hexane, then ethyl acetate to give the title compound as a foam (5.92 g, 93%); v$_{max}$ (CH$_2$Cl$_2$) 3418, 1751, 1677, 1612, 1514 and 1465 cm$^{-1}$; m/z (FAB, +ve ion, 3-nitrobenzyl alcohol/sodium acetate) 731 (MNa+).

k) 4-Methoxybenzyl (6R,7S)-7-Phenylacetamido-3-[(S)-tetrahydrofuran-2-yl]-1-carba-1-dethiaceph-3-em-4-carboxylate A solution of the phosphorane (5.90 g, 8.33 mmol) and benzoic acid (20 mg) in toluene (100 ml) was heated at reflux for 10 h. The reaction mixture was cooled, concentrated and the residue purified by chromatography on silica gel eluting with 50, then 70% ethyl acetate in hexane yielding the title compound as a yellow foam (3.54 g, 87%); $[\alpha]_D$–40.6° (c 1.0 CHCl$_3$); (Found: M$^+$490.2096. C$_{28}$H$_{30}$N$_2$O$_6$ requires M 490.2104); v$_{max}$ (CHCl$_3$) 3416, 1766, 1716, 1677, 1613, 1516 and 1394 cm$^{-1}$; δ$_H$(CDCl$_3$) 1.12 (1H, m), 1.50 (1H, m), 1.83–1.96 (3H, m), 2.18–2.43 (3H, m), 3.57 and 3.65 (2H, ABq, J 16.1 Hz), 3.76–3.90 (3H, m), 3.79 (3H, s), 4.92 (1H, dd, J 8.9, 6.8 Hz), 5.10 and 5.19 (2H, ABq, J 11.9 Hz), 5.26 (1H, m), 5.86 (1H, d, J 6.8 Hz), 6.88 (2H, d, J 8.7 Hz) and 7.20–7.32 (7H, m).

l) 4-Methoxybenzyl (6R,7S)-7-amino-3-[(S)-tetrahydrofuran-2-yl]-1-carba-1-dethiaceph-3-em-4-carboxylate A solution of 4-methoxybenzyl (6R,7S)-7-phenylacetamido-3-[(S)-tetrahydrofuran-2-yl]-1-carba-1-dethiaceph-3-em-4-carboxylate (3.53 g, 7.20 mmol) and N-methylmorpholine (1.6 ml, 14.6 mmol) in dichloromethane (100 ml) was treated with phosphorus pentachloride (2.25 g, 10.80 mmol) in dichloromethane (56 ml) at −25° C. The reaction was stirred at −10°±5° C. for 45 min., then methanol (15 ml) was added, and stirring continued for 45 min. at room temperature. Water (32 ml) was then added, and the mixture vigorously stirred for a further 1 h. The dichloromethane was evaporated in vacuo, and the aqueous residue adjusted to pH7 with concentrated ammonia solution in the presence of ethyl acetate. The mixture was extracted twice with ethyl acetate, dried and concentrated in vacuo. The residue was purified by chromatography on silica gel eluting with ethyl acetate, then 5% methanol in ethyl acetate yielding the title compound as a pale yellow foam (1.53 g, 57%); $[\alpha]_D$−114.3 (c 1.0 CHCl$_3$); $\nu_{max}$ (CH$_2$Cl$_2$) 1760, 1717, 1614 and 1516 cm$^{-1}$; $\delta_H$ (CDCl$_3$), 1.34−2.45 (10H, m, 2H exch.), 3.68−3.96 (3H, m), 3.80 (3H, s), 4.46 (1H, d, J 5.4 Hz), 4.94 (1H, dd, J 8.9, 6.8 Hz), 5.13 and 5.20 (2H, ABq, J 12.0 Hz), 6.89 (2H, d, J 8.6 Hz) and 7.36 (2H, d, J 8.6 Hz); m/z (CI, +ve ion, ammonia) 373 (MH+).

m) 4-Methoxybenzyl (6R,7S)-7-[2-(2-aminothiazol-4-yl)-2-(Z)-methoxyiminoacetamido]-3-[(S)-tetrahydrofuran-2-yl]-1-carba-1-dethiaceph-3-em-4-carboxylate Methanesulphonyl chloride (350 μl, 4.52 mmol) was added to 2-(2-thiazol-4-yl)-2-(Z)-methoxyiminoacetic acid (909 mg, 4.52 mmol) and N,N-diisopropylethylamine (788 μl, 4.52 mmol) in DMF (15 ml) at −30° C. After stirring at −30°±10° C. for 30 min., a solution of 4-methoxybenzyl (6R,7S)-7-amino-3-[(S)-tetrahydrofuran-2-yl]-1-carba-1-dethiaceph-3-em-4-carboxylate (1.52 g, 4.10 mmol) in DMF (6 ml) was added, followed by pyridine (366 μl, 4.52 mmol). The reaction mixture was transferred to an ice-bath and stirring continued for a further 1 h. After dilution with ethyl acetate, the solution was washed successively with saturated sodium hydrogen carbonate solution, 5% aqueous citric acid, water (×2) and brine, dried and then concentrated in vacuo. The residue was purified by chromatography on silica gel eluting with ethyl acetate to give the title compound as a pale yellow foam (1.82 g, 80%); $[\alpha]_D$+51.5 (c 1.0 CHCl$_3$); $\nu_{max}$ (CH$_2$Cl$_2$) 3478, 1755, 1718, 1675, 1614, 1531 and 1516 cm$^{-1}$; $\delta_H$ (CDCl$_3$) 1.50−1.79 (2H, m), 1.84−1.97 (2H, m), 2.08−2.50 (4H, m), 3.81 (3H, s), 3.82−3.96 (3H, m), 3.98 (3H, s), 4.96 (1H, m), 5.17 (2H, s), 5.65 (1H, dd, J7.9, 5.0 Hz), 5.93 (2H, br.s, exch.), 6.72 (1H, s), 6.89 (2H, d, J 8.6 Hz), 7.34 (2H, d, J 8.6 Hz) and 8.48 (1H, br.s); m/z (FAB, +ve ion thioglycerol) 556 (MH+).

n) Sodium (6R,7S)-7-[2-(2-aminothiazol-4-yl)-2-(Z)-methoxyiminoacetamido]-3-[(S)-tetrahydrofuran-2-yl]-1-carba-1-dethiaceph-3-em-4-carboxylate Aluminium chloride (58 mg, 0.44 mmol) was added to anisole (2.3 ml) and dry dichloromethane (1.3 ml) at −20° C. and stirred for 15 min. The temperature of the cooling bath was then lowered to −40° C. before addition of 4-methoxybenzyl (6R,7S)-7-[2-(2-aminothiazol-4-yl)-2-(Z)-methoxy-iminoacetamido]-3-[(S)-tetrahydrofuran-2-yl]-1-carba-1-dethiaceph-3-em-4-carboxylate (80 mg, 0.14 mmol) in dichloromethane (5 ml). After 10 min., the solution was treated with trisodium citrate (0.5M, 4.5 ml) and then vigorously stirred for 10 min. at room temperature. The aqueous phase was separated, washed twice with dichloromethane and concentrated in vacuo. The residue was chromatographed on HP20SS eluting with water, 1%, then 2% THF in water. Fractions containing the product (h.p.l.c. analysis) were combined, concentrated and freeze-dried to give the title compound (42mg, 66%); $\nu_{max}$ (KBr) 1745, 1659, 1594, 1531 and 1386 cm$^{-1}$; $\delta_H$ (d$_6$-DMSO) 1.42−1.56 (2H, m), 1.72−1.90 (3H, m), 2.02−2.16 (3H, m), 3.55−3.80 (3H, m), 3.83 (3H, s), 4.95 (1H, m), 5.23 (1H, dd, J 8.6, 4.9 Hz), 6.73 (1H, s), 7.22 (2H, br.s, exch.) and 9.19 (1H, d, J 8.6Hz); m/z (FAB, +ve ion, thioglycerol) 458 (MH+).

o) Pivaloyloxymethyl (6R,7S)-7-[2-(2-aminothiazol-4-yl)-2-(Z)-methoxyiminoacetamido]-3-[(S)-tetrahydrofuran-2-yl]-1-carba-1-dethiaceph-3-em-4-carboxylate Pivaloyloxymethyl bromide (343mg, 1.76 mmol) in N-methylpyrrolidin-2-one (4 ml) was added dropwise over 1 h to a solution of sodium (6R,7S)-7-[2-(2-aminothiazol-4-yl)-2-(Z)-methoxyiminoacetamido]-3-[(S)-tetrahydrofuran-2-yl]-1-carba-1-dethiaceph-3-em-4-carboxylate (200mg, 0.44 mmol) in N-methylpyrrolidin-2-one (10 ml) containing finely powdered potassium carbonate (12 1 mg, 0.95 mmol). After stirring for 30 min., the mixture was diluted with ethyl acetate, washed twice with water and brine, dried and concentrated. The residue was purified by chromatography on silica gel eluting with 50% ethyl acetate in hexane, then ethyl acetate to give the title compound as a colourless foam (115 mg, 48%); $[\alpha]_D$+65.4° (c 1.0 CHCl$_3$); (Found: M$^+$549.1911. C$_{24}$H$_{31}$N$_5$O$_8$S requires 549.1893); $\nu_{max}$(CH$_2$Cl$_2$) 3486, 1758, 1674, 1622, 1531 and 1387 cm$^{-1}$; $\delta_H$ (CDCl$_3$) 1.23 (9H, s), 1.50−1.72 (2H, m), 1.92−2.52 (6H, m), 3.71−3.90 (3H, m), 4.00 (3H, s), 4.93 (1H, dd, J 8.8, 6.9 Hz), 5.64 (1H, dd, J 7.7, 5.0 Hz), 5.66 and 5.82 (2H, ABq, J 5.6 Hz), 6.02 (2H, br.s, exch.), 6.77 (1H, s), and 8.29 (1H, d, J 7.7 Hz).

EXAMPLE 2 Route 2

4-Methoxybenzyl (6R,7S)-7-phenylacetamido-3-[(R and S)-tetrahydrofuran-2-yl]-1-carb-1-dethiaceph-3-em-4-carboxylate a) (3S,4R)4-[(2,2-Dimethyl-4H-1,3-dioxin-4-on-6-yl)ethenyl]-1-(4-methoxyphenyl)-3-phenylacetamidoazetidin-2-one A suspension of (3S,4S)-4-formyl-1-(4-methoxyphenyl)-3-phenylacetamidoazetidin-2-one (10.18 g, 30.1 mmol) in acetonitrile (450 ml) was treated with 2,2-(dimethyl)-6-[(triphenylphosphoranylidene)methyl]-4H-1,3-dioxin-4-one (12.5 g, 31.1 mmol) and stirred at room temperature for 3 days. The reaction mixture was concentrated in vacuo and the residue purified by flash chromatography on silica gel eluting with ethyl acetate to yield the title compound as a yellow foam (12.40 g, 89%); $[\alpha]_D$−127.5° (c 1.0 CHCl$_3$); $\nu_{max}$ (CH$_2$Cl$_2$) 3416, 1756, 1724, 1683 and 1513 cm$^{-1}$; $\delta_H$ (CDCl$_3$) 1.72 (3H, s), 1.73 (3H, s), 3.59 (2H, s), 3.77 (3H, s), 4.88 (1H, dd, J 6.0, 5.4 Hz), 5.27 (1H, s), 5.44 (1H, dd, J 7.8, 5.4 Hz), 6.02 (1H, d, J 15.8 Hz), 6.17 (1H, d, J 7.8 Hz), 6.42 (1H, dd, J 15.8, 6.1 Hz), 6.83 (2H, d, J 9.0 Hz) and 7.17−7.33 (7H, m); m/z (FAB, +ve ion, 3-nitrobenzyl alcohol/sodium acetate) 485(MNa$^+$).

b) (3S,4R)-4-[(2,2-Dimethyl-4H-1,3-dioxin-4-on-6-yl)ethyl]-1-(4-methoxyphenyl)-3-phenylacetamidoazetidin-2-one A solution of (3S,4R)-4-[(2,2-dimethyl)-4H-1,3-dioxin-4-on-6-yl)ethenyl]-1-(4-methoxyphenyl)-3-phenylacetamidoazetidin-2-one (12.4 g, 26.8 mmol) in tetrahydrofuran (250m1) was hydrogenated over 10% palladium on carbon (1.2 g) for 3h. After filtration through a pad of celite, the filtrate was concentrated to yield the title compound (12.07 g, 97%); $\nu_{max}$(CH$_2$Cl$_2$) 3416, 1747, 1726, 1684 and 1514 cm$^{-1}$; $\delta_H$ (CDCl$_3$) 1.67 (3H, s), 1.68 (3H, s), 2.02–2.15 (4H, m), 3.63 (2H, s), 3.77 (3H, s), 4.21 (1H, m), 5.13 (1H, s), 5.35 (1H, dd, J 7.6, 5.0 Hz), 6.77 (1H, d, J7.6 Hz), 6.81 (2H, d, J 9.0 Hz), 7.19 (2H, d, J 9.0 Hz) and 7.23–7.40 (5H, m); m/z (FAB, +ve ion, 3-nitrobenzyl alcohol/sodium acetate) 487 (MNa$^+$).

c) (3S,4R)-4-[(2,2-Dimethyl)-4H-1,3-dioxin-4-on-6-yl)ethyl]-3-phenylacetamidoazetidin-2-one A suspension of (3S,4R)-4-[(2,2-dimethyl-4H-1,3-dioxin-4-on-6-yl)ethyl]-1-(4-methoxyphenyl)-3-phenylacetamidoazetidin-2-one (10.58 g, 22.80 mmol) in tetrahydrofuran (425 ml) was treated with a solution of ceric ammonium nitrate (40.0 g, 73.0 mmol) in water (245 ml) at 0° C. After stirring for 10 min. at 0° C., the reaction mixture was diluted with ethyl acetate and the aqueous phase extracted four times with a mixture of tetrahydrofuran and ethyl acetate (2:1). The combined organic extracts were washed successively with 5% aqueous sodium hydrogen carbonate solution, 10% aqueous sodium sulphite solution (×3), 5% aqueous sodium hydrogen carbonate solution, water and then brine. After drying over magnesium sulphate, the solvent was evaporated in vacuo to yield the crude title compound (7.50 g, 92%); $\nu_{max}$ (CH$_2$Cl$_2$) 3410, 1771, 1725, 1684, 1636 and 1512 cm$^{-1}$; $\delta_H$ (CDCl$_3$) 1.62–1.75 (2H, m), 1.65 (6H, s), 2.12–2.21 (2H, m), 3.95 (2H, s), 3.80 (1H, m), 5.05 (1H, br.s, exch.), 5.25 (1H, m), 5.29 (1H, s), 6.78 (1H, d, J 7.9 Hz) and 7.21–7.38 (5H, m); m/z (FAB, –ve ion, thioglycerol) 357 (M–H)$^-$.

d) 4-Methoxybenzyl 3-oxo-5-[(3S,4R)-3-phenylacetamidoazetidin-2-on-4-yl]pentanoate A solution of 4-methoxybenzyl alcohol (1.50 g, 10.87 mmol) in toluene (6 ml) was added to a solution of (3S,4R)-4-[(2,2-dimethyl-4H-1,3-dioxin-4-on-6-yl)ethyl]-3-phenylacetamidoazetidin-2-one (3.86 g, 10.78 mmol) and heated to reflux for 1.5 h. The reaction mixture was concentrated in vacuo and the residue triturated with toluene to give the title compound (3.50 g, 75%) as a crude product; $\nu_{max}$ (CH$_2$Cl$_2$) 3412, 1772, 1747, 1717, 1684 and 1514 cm$^{-1}$; $\delta_H$ (CDCl$_3$) 1.63 (2H, m), 2.39 (2H, t, J7.0 Hz), 3.37 (2H, s), 3.58 (2H, s), 3.68 (1H, m), 3.81 (3H, s), 5.09 (2H, s), 5.18 (1H, m), 6.26 (1H, br.s, exch.), 6.63 (1H, d, J 7.9 Hz), 6.89 (2H, d, J 8.6 Hz) and 7.21–7.38 (7H, m); m/z (FAB, –ve ion, thioglycerol) 437 (M–H)$^-$.

e) 4-Methoxybenzyl 2-diaza-3-oxo-5-[(3S,4R)-3-phenylacetamidoazetidin-2-on-4-yl]pentanoate A solution of 4-methoxybenzyl 3-oxo[(3S,4R)-3-phenylacetamidoazetidin-2-on-4-yl]pentanoate (3.508, 8.0 mmol) in acetonitrile (150 ml) was treated with 4-toluenesulphonyl azide (2.21 g, 11.22 mmol) and N,N-diisopropylethylamine (2.1 ml, 12.08 mmol) at 0° C. After 10 min., the ice-bath was removed and stirring was continued at room temperature for 2h. The reaction mixture was diluted with ethyl acetate and washed with brine. After drying over magnesium sulphate, the solvent was evaporated in vacuo and the residue purified by chromatography on silica gel eluting with 50% ethyl acetate in hexane, then ethyl acetate to yield the title compound (2.94 g, 79%); $[\alpha]_D$+33.6° (c 1.0 CHCl$_3$); $\nu_{max}$(CH$_2$Cl$_2$) 3410, 2142, 1770, 1713, 1683 and 1515 cm$^{-1}$; $\delta_H$ (CDCl$_3$) 1.59–1.78 (2H, m), 2.67–2.92 (2H, m), 3.57 and 3.64 (2H, ABq, J 15.6 Hz), 3.78 (1H, m), 3.81 (3H, s), 5.18 (2H, s), 5.24 (1H, m), 6.37 (1H, br.s, exch.), 6.59 (1H, d, J 8.2 Hz), 6.91 (2H, d, J 8.7 Hz), and 7.23–7.36 (7H, m); m/z (CI, +ve ion, ammonia) 465 (MH$^+$).

f) 4-Methoxybenzyl (6R,7S)-7-phenylacetamido-3-(trifluoromethylsulfonyloxy)-1-carba-1-dethiaceph-3-em-4-carboxylate A solution of 4-methoxybenzyl 2-diazo-3-oxo-5-[(3S,4R)-3-phenylacetamidoazetidin-2-on-4-yl]pentanoate (2.90 g, 6.25 mmol) in chloroform (75 ml) was heated to reflux in the presence of a catalytic quantity of rhodium (II) acetate dimer. After heating for 1 h, the reaction mixture was cooled to 0° C. and treated sequentially with N,N-diisopropylethylamine (2.2 ml, 12.51 mmol) and trifluoromethanesulphonic anhydride (1.16 ml, 6.90 mmol). After stirring for 30 min. at 0° C., the mixture was concentrated in vacuo. The residue was purified by chromatography on silica gel eluting with 30, then 50% ethyl acetate in hexane yielding the title compound as an orange foam (1.80 g, 51%); $[\alpha]_D$+24.1° (c 1.0 CHCl$_3$); $\nu_{max}$ (CH$_2$Cl$_2$) 3416, 1783, 1734, 1685 and 1516 cm$^{-1}$; $\delta_H$ (CDCl$_3$) 1.45 (1H, m), 1.98 (1H, m), 2.56 (2H, m), 3.60 (2H, s), 3.79 (3H, s), 3.87 (1H, m), 5.13–5.32 (3H, m), 6.06 (1H, d, J 6.3 Hz), 6.86 (2H, d, J 8.7 Hz) and 7.21–7.40 (7H, m); m/z (CI, +ve ion, ammonia) 586 (MNH$_4^+$).

g) 4-Methoxybenzyl (6R,7S)-7-phenylacetamido-3-[(S)-tetrahydrofuran-2-yl]-1-carba-1-dethiaceph-3-em-4-carboxylate A solution of (tetrahydrofuran-2-yl)tri-n-butylstannane (J. S. Sawyer, A. Kucerovy, T. L. MacDonald and G. J. McGarvey, *J. Amer. Chem. Soc.*, 1988, 110, 842) (1.89 g, 5.24 mmol) in THF (10 ml) was cooled to –78° C. n-Butyl lithium (3.53 ml of a 1.48M solution in hexane, 5.22 mmol) was then added and the solution was stirred for 15 min. at –78° C. A second flask containing copper (I) bromide dimethylsulphide complex (538 mg, 2.62 mmol) suspended in a mixture of dimethyl sulphide (8 ml) and THF (16 ml) was then cooled to –78° C. The α-lithiotetrahydrofuran species was transferred via a cannula to the suspension of copper bromide at –78° C. The red-brown homogeneous solution was stirred for 30 min. at –78° C. A third flask containing a solution of 4-methoxybenzyl (6R,7S)-7-phenylacetamido-3-(trifluoromethylsulfonyloxy)-1-carba-1-dethiaceph-3-em-4-carboxylate (900 mg, 1.58 mmol) in THF (12 ml) was then cooled to –78° C. The cuprate species was transferred via a cannula to the solution of triflate at –78° C. The reaction mixture was stirred for 1.5 h at –78° C., then quenched by the addition of saturated aqueous ammonium chloride (16 ml). The resulting mixture was allowed to warm to room temperature then diluted with water and extracted twice with ethyl acetate. The combined organic phases were washed with water, brine, then dried over magnesium sulphate. After removal of the solvents in vacuo, the residue was purified by chromatography on silica gel eluting with 10, 20 and 30% ethyl acetate in dichloromethane. The title compound was obtained as a mixture of diastereoisomers (300 mg, 39%); $\nu_{max}$ (CH$_2$Cl$_2$) 3418, 1769, 1718, 1684 and 1516 cm$^{-1}$; $\delta_H$ (CDCl$_3$) 1.10–2.68 (8H, m), 3.61 (2H, s), 3.72–3.91 (3H, m), 3.79 (3H, s), 4.93 and 5.09 (together 1H, 2m), 3.79 (3H, s), 4.93 and 5.09 (together 1H, 2m), 5.13–5.28 (3H, m), 5.93 and 5.98 (together 1H, 2d, J 7.9 Hz), 6.87 (2H, d, J 8.6 Hz) and 7.22–7.39 (7H, m); m/z (CI, +ve ion, ammonia) 491 (MH$^+$).

EXAMPLE 3 Route A

4-Methoxybenzyl (6R,7S)-7-phthalimido-3-[(S)-tetrahydrofuran-2-yl]-1-carba-1-dethiaceph-3-em-4-carboxylate a) (3S,4S)-4-Formyl-1-(4-methoxyphenyl)-3-phthalimidoazetidin-2-one Aqueous 50% w/w periodic acid (6.3 ml, 22 mmol) was added to (3S,4S)-4-[(4R)-2,2-dimethyl-1,3-dioxolan-4-yl]-1-(4-methoxyphenyl)-3-phthalimido-azetidin-2-one (4.22 g, 10 mmol) in 50% aqueous THF (75 ml) and heated under reflux for 2.5h. The cooled solution was extracted twice with ethyl acetate and the combined extracts washed twice with water then with brine, dried and evaporated to give a colourless solid. The solid was triturated with ether and the title compound filtered off and dried in vacuo (3.151 g, 90%); [α]$_D$−214.3° (c=1.00 CHCl$_3$); ν$_{max}$ (CHCl$_3$) 1785 (sh), 1769, 1727, 1514, 1391, 1250, and 1124 cm$^{-1}$; δ$_H$ (CDCl$_3$) 3.73 (3H, s), 4.77 (1H, dd, J 6.29, 2.78 Hz), 5.80 (1 H, d, J 5.80 Hz), 6.95 and 7.39 (4H, ABq, J 8.97 Hz), 7.7–8.0 (4H, m) and 9.90 (1H, d, J 2.73 Hz); m/z (EI) 350 (14), 149 (100%).

b) (3S,4R)-1-(4-Methoxyphenyl)-4-[3-oxo-4-[(S)-tetrahydrofuran-2-yl]-propenyl]-3-phthalimidoazetidin-2-one (3S,4S)-4-Formyl-1-(4-methoxyphenyl)-3-phthalimidoazetidin-2-one (3.309 g, 9.45 mmol) and (S)-tetrahydrofuran-2-ylcarbonylmethylene-phosphorane (4.193 g, 11 mmol) in acetonitrile (100 ml) were stirred for 48 h then heated under reflux for 1.5 h. The mixture was concentrated and flash chromatographed on silica gel eluting with 50–60% ethyl acetate in hexane to give the product contaminated with triphenylphosphine oxide. Flash chromatography on silica gel eluting with ethyl acetate gave the title compound as a foam (3.646 g, 87%); [α]$_D$−55.0° (c=1.00 CHCl$_3$); (Found: M$^+$446.1481. C$_{25}$H$_{22}$N$_2$O$_6$ requires M 446.1478); ν$_{max}$(CHCl$_3$) 1785, 1760, 1726, 1514, 1386 and 1249 cm$^{-1}$; δ$_H$(CDCl$_3$) 1.5–2.2 (4H, m), 3.65–3.85 (2H, m), 3.81 (3H, s), 4.39 (1H, dd, J 8.32, 5.93 Hz), 5.03 (1H, t, J 6.09 Hz), 5.70 (1H, d, J 5.63 Hz), 6.63 (1H, d, J 16.18 Hz), 6.85–7.0 (3H, m), 7.38 (2H, d, J 9.00 Hz) and 7.7–7.9 (4H, m); m/z (FAB, +ve ion, thioglycerol) 447 (MH$^+$).

c) (3S,4R)-1-(4-Methoxyphenyl)-4-[3-oxo-4-[(S)-tetrahydrofuran-2-yl]propyl]-3-phthalimidoazetidin-2-one (3S,4R)-1-(4-Methoxyphenyl)-4-[3-oxo-4-[(S)-tetrahydrofuran-2-yl]-propenyl]-3-phthalimidoazetidin-2-one (3.646 g) in THF (50 ml) was hydrogenated in the presence of 10% palladium on carbon (200 mg) until hydrogen uptake ceased, required ~2 h. The catalyst was filtered off and the filtrate concentrated in vacuo then flash chromatographed on silica gel eluting with 50–70% ethyl acetate in hexane to give the title compound (3.036 g, 83%); [α]$_D$+48.7° (c=1.00 CHCl$_3$); (Found: M$^+$448.1628. C$_{25}$H$_{24}$N$_2$O$_6$ requires M 448.1634); ν$_{max}$ (CHCl$_3$) 1785, 1753, 1724, 1514, 1386, 1248 and 1220 cm$^{-1}$; δ$_H$ (CDCl$_3$) 1.7–2.55 (8H, m), 3.7–3.85 (2H, m), 3.82 (3H, m), 4.15–4.25 (1H, m), 4.3–4.45 (1H, m), 5.47 (1H, d, J 5.18 Hz), 6.94 and 7.51 (4H, ABq, J 8.92 Hz) and 7.7–8.0 (4H, m); m/z (CI, +ve ion, ammonia) 449 (MH$^+$), 466 (MNH$_4^+$).

d) (3S,4R)-4-[3-Oxo-4-[(S)-tetrahydrofuran-2-yl]propyl]-3-phthalimidoazetidin-2-one Ceric ammonium nitrate (11.141 g, 20.3 mmol) in water (60 ml) was added dropwise to (3S,4R)-1-(4-methoxyphenyl)-4-[3-oxo-4-[(S)-tetrahydrofuran-2-yl]propyl]-3-phthalimidoazetidin-2-one (3.036 g, 6.8 mmol) in THF (100 ml) cooled in an ice-salt bath. TLC after ~40 ml of the ceric ammonium nitrate solution had been added showed no starting material so the addition was stopped, the reaction stirred 0.25 h then ethyl acetate (20 ml) added and the organic layer collected. The aqueous solution was extracted twice with ethyl acetate (50 ml) then the combined ethyl acetate solutions washed successively with 5% sodium bicarbonate, 10% sodium sulphite twice, 5% sodium bicarbonate and brine, dried and evaporated to give the title compound as a foam (2.234 g, 88%); [α]$_D$+6.3° (c=1.00 CHCl$_3$); ν$_{max}$ (CHCl$_3$) 1794, 1769, 1727, 1512, 1389 and 1219 cm$^{-1}$; δ$_H$ (CDCl$_3$) 1.7–2.2 (6H, m), 2.4–2.8 (2H, m), 3.7–4.0 (3H, m), 4.2–4.3 (1H, m), 5.41 (1H, d, J 5.07 Hz), 6.54 (1H, s) and 7.7–7.95 (4H, m); m/z (CI, +ve ion, ammonia) 343 (MH$^+$), 360 (MNH$_4^+$).

e) 4-Methoxybenzyl (RS)-2-hydroxy-2-[(3S,4R)-4-[(S)-tetrahydrofuran-2-yl]propyl]-3-phthalimidoazetidin-2-on-1-yl]acetate 4-Methoxybenzyl glyoxylate hydrate (1.647 g, 8.5 mmol) in 1,2-dichloroethane (40 ml) was heated under a Dean and Stark trap for heavy entrainers containing 4A molecular sieves for 0.75h. The solution was allowed to cool then (3S,4R)-4-[3-oxo-4-[(S)-tetrahydrofuran-2-yl]propyl]-3-phthalimidoazetidin-2-one (2.234 g, 6.5 mmol) in dichloromethane (20 ml) followed by methylamine (90 µl, 0.65 mmol) were added. The reaction was stirred 0.5 h then concentrated and flash chromatographed on silica gel eluting with 30–90% ethyl acetate in hexane to give the title compound (2.592 g, 74%); [α]$_D$+28.40 (c=1.00 CHCl$_3$); ν$_{max}$(CHCl$_3$) 3685, 3518, 1772, 1725, 1516, 1385 and 1087 cm$^{-1}$; m/z (CI, +ve ion, ammonia) 554 (MNH$_4^+$); (FAB, +ve ion, 3-nitrobenzyl alcohol/sodium acetate) 559 (MNa$^+$).

f) 4-Methoxybenzyl 2-[(3S,4R)-4-[3-oxo-3-[(S)-tetrahydrofuran-2-yl]propyl]-3-phthalimidoazetidin-2-on-1-yl]-2-tri-n-butylphosphoranylideneacetate A solution of thionyl chloride (530 µl, 7.27mmol) in THF (3 ml) was added to 4-methoxybenzyl (RS)-2-hydroxy-2-[(3S, 4R)-4-[3-oxo-3-[(S)-tetrahydrofuran-2-yl]propyl]-3-phthalimidoazetidin-2-on-1-yl]acetate (2.59 g, 4.84 mmol) and 2,6-lutidine (850 µl, 7.30 mmol) in THF (50 ml) at −20° C. After stirring for 1 h, the reaction mixture was filtered through a pad of celite, and the filtrate evaporated in vacuo. Toluene was added and re-evaporated to yield 4-methoxybenzyl (RS)-2-chloro-2-[(3S,4R)-4-[3-oxo-3-[(S)-tetrahydrofuran-2-yl]propyl]-3-phthalimidoazetidin-2-on-1-yl]acetate.

The crude chloro compound was dissolved in dioxan (20 ml) and treated with tri-n-butylphosphine (2.65 ml, 10.63 mmol). After stirring for 30 min. at room temperature, the reaction mixture was diluted with ethyl acetate and washed successively with hydrochloric acid (0.5M), dilute sodium hydrogen carbonate solution, water and brine. The organic solution was dried, concentrated and then chromatographed on silica gel eluting with 30, 50 and 70% ethyl acetate in hexane to give the title compound as a yellow oil (2.90 g, 83%); (Found: M$^+$720.3553. C$_{40}$H$_{53}$N$_2$O$_8$P requires M 720.3540); ν$_{max}$(CH$_2$Cl$_2$) 1755, 1721, 1613, 1514 and 1387 cm$^{-1}$.

g) 4-Methoxybenzyl (6R,7S)-7-Phthalimido-3-[(S)-tetrahydrofuran-2-yl]-1-carba-1-dethiaceph-3-em-4-carboxylate A solution of 4-methoxybenzyl 2-[(3S,4R)4-[3-oxo-3-[(S)-tetrahydrofuran-2-yl]propyl]-3-phthalimidoazetidin-2-on-1-yl]-2-tri-n-butylphosphoranylideneacetate (2.90 g, 4.03 mmol) and benzoic acid 920 mg) in toluene (50 ml) was heated to reflux for 10h. The reaction mixture was cooled, concentrated and the residue purified by chromatography on silica gel eluting with 30, then 50% ethyl acetate in hexane yielding the title compound as a colourless foam (1.77 g, 88%); [α]$_D$−76.6° (c 1.0 CHCl$_3$); (Found: M$^+$502.1734. C$_{28}$H$_{26}$N$_2$O$_7$ requires M 502.1740); ν$_{max}$ (CH$_2$Cl$_2$) 1772, 1724, 1613, 1516 and 1386 cm$^{-1}$; δ$_H$ (CDCl$_3$) 1.60 (1H, m), 1.86–1.99 (4H, m), 2.28–2.42 (3H, m), 3.80 (3H, s), 3.82–3.95 (3H, m), 5.00 (1H, dd, J 8.9, 6.9 Hz), 5.17 and 5.24 (2H, ABq, J 11.9 Hz), 5.59 (1H, d, J 5.1 Hz), 6.88 (2H, d, J 8.7 Hz), 7.39 (2H, d, J 8.7 Hz), 7.75–7.80 (2H, m) and 7.84–7.89 (2H, m).

EXAMPLE 4

Sodium (6R,7S)-7-[2-(2-aminothiazol-4-yl)-2-(Z)-prop-2-yloxyimino-acetamido]-3-[(2S)-tetrahydrofuran-2-yl]-1-carba-1-dethiaceph-3-em-4-carboxylate a) 4-Methoxybenzyl (6R,7S)-7-[2-(2-aminothiazol-4-yl)-2-(Z)-prop-2-yloxyiminoacetamido]-3-[(2S)-tetrahydrofuran-2-yl]-1-carba-1-dethiaceph-3-em-4-carboxylate 2-(2-Aminothiazol-4-yl)-2-(Z)-prop-2-yloxyiminoacetic acid (52mg, 2.27mmol) in DMF (2 ml) was treated with methanesulphonyl chloride (17 µl, 2.20 mmol) and N-N-diisopropylethylamine (39 µl, 2.24 mmol) as described in Example 1(m). This was then treated successively with a solution of 4-methoxybenzyl (6R, 7S)-7-amino-3-[(2S)-tetrahydrofuran-2-yl]-1-carba-1-dethiaceph-3-em-4-carboxylate (70 mg, 1.88 mmol) in DMF (2 ml) and pyridine (18 µl, 2.23 mmol). After work-up the product was purified by chromatography on silica gel eluting with 50, 70 and 100% ethyl acetate in hexane to yield the title compound as a colourless foam (85 mg, 78%); $v_{max}$ (CH$_2$Cl$_2$) 3482, 1768, 1718, 1680, 1608, 1516 and 1390 cm$^{-1}$; $\delta_H$ (CDCl$_3$) 1.26 (3H, d, J 6.2 Hz), 1.29 (3H, d, J 6.2 Hz), 1.42–2.55 (8H, m), 3.81 (3H, s), 3.82–3.98 (3H, m), 4.56 (1H, sept, J 6.2 Hz), 4.97 (1H, dd, J 8.9, 6.8 Hz), 5.18 (2H, s), 5.28 (2H, br.s, exch.), 5.43 (1H, dd, J 6.7, 4.9 Hz), 6.88 (2H, d, J 8.6 Hz), 6.89 (1H, s), 7.02 (1H, br.d, J 6.7 Hz) and 7.35 (2H, d, J 8.6 Hz); m/z (CI, +ve ion, ammonia) 584 (MH$^+$).

b) Sodium (6R,7S)-7-[2-(2-aminothiazol-4-yl)-2-(Z)-prop-2-yloxyiminoacetamido]-3-[(2S)-tetrahydrofuran-2-yl]-1-carba-1-dethiaceph-3-em-4-carboxylate A solution of 4-methoxybenzyl (6R,7S)-7-[2-(2-aminothiazol-4-yl)-2-(Z)-prop-2-yloxyiminoacetamido]-3-[(2S)-tetrahydrofuran-2-yl]-1-carba-1-dethiaceph-3-em-4-carboxylate (85 mg; 0.15 mmol) in dichloromethane (5 ml) was added to a solution of aluminium chloride (58 mg, 0.44 mmol) in anisole (2.4 ml) and dichloromethane (1.3 ml) as described in Example 1 (n). After quenching with trisodium citrate (0.5M, 4.5 ml) and subsequent work-up, the product was purified by chromatography on HP20SS eluting with water, then 1,2,4 and 5% THF in water. Fractions containing the product (h.p.l.c. analysis) were combined and freeze-dried to give the title compound (35 mg, 49%); $v_{max}$ (KBr) 1745, 1659, 1594, 1532 and 1385 cm$^{-1}$; $\delta_H$ (d$_6$-DMSO) 1.18 (3H, d, J 6.2 Hz), 1.20 (3H, d, J 6.2 Hz), 1.41–1.60 (2H, m), 1.75–1.88 (3H, m), 2.01–2.14 (3H, m), 3.53–3.80 (3H, m), 4.29 (1H, sept, J 6.2 Hz), 4.92 (1H, dd, J 8.7, 6.8 Hz), 5.20 (1H, dd, J 8.4, 4.9 Hz), 6.70 (1H, s), 7.23 (2H, br.s, exch.) and 9.15 (1H, d, J 8.4 Hz); m/z (FAB, +ve ion, thioglycerol) 486 (MH$^+$).

EXAMPLE 5

Sodium (6R,7S)-7-[2-(2-aminothiazol-4-yl)-2-(Z)-hydroxyimino-acetamido]-3-[(2S)-tetrahydrofuran-2-yl]-1-carba-1-dethiaceph-3-em-4-carboxylate a) 4-Methoxybenzyl (6R,7S)-7-[2-(2-Tritylaminothiazol-4-yl)-2-[(Z)-2-methoxyprop-2-yloxyimino]acetamido]-3-[(2S)-tetrahydrofuran-2-yl]-1-carba-1-dethiaceph-3-em-4-carboxylate 2-Methoxypropene (93 µl, 0.97 mmol) was added to a suspension of (Z)-2-hydroxyimino-2-(2-tritylamino-4-thiazol)acetic acid (138 mg, 0.32 mmol) in dichloromethane (3 ml) at 10° C. The mixture was stirred for 30 min at room temperature and then concentrated to give 2-(2-tritylaminothiazol-4-yl)-2-[(Z)-2-methoxyprop-2-yloxyimino]acetic acid.

The crude acid in DMF (2 ml) was treated with methanesulphonyl chloride (25 µl, 0.32 mmol) and N,N-diisopropylethylamine (56 µl, 0.32 mmol) as described in Example 1(m). This was then treated successively with a solution of 4-methoxybenzyl (6R,7S)-7-amino-3-[(2S)-tetrahydrofuran-2-yl]-1-carba-1-dethiaceph-3-em-4-carboxylate (100 mg, 0.27 mmol) in DMF (2 ml) and pyridine (26 µl, 0.32 mmol). After work-up the product was purified by chromatography on silica gel eluting with 30 and then 50% ethyl acetate in hexane to yield the title compound as a colourless foam (166 mg, 72%); $v_{max}$ (CH$_2$Cl$_2$) 3400, 1770, 1732, 1685, 1612, 1516 and 1374 cm$^{-1}$; $\delta_H$ (CDCl$_3$) 1.42–2.52 (8H, m), 1.50 (3H, s), 1.53 (3H, s), 3.25 (3H, s), 3.81 (3H, s), 3.82–3.95 (3H, m), 4.96 (1H, dd, J9.0, 6.8 Hz), 5.18 (2H, s), 5.34 (1H, dd, J 6.0, 5.3 Hz), 6.41 (1H, d, J 6.0 Hz), 6.73 (1H, s), 6.83 (1H, s), 6.89 (2H, d, J 8.7 Hz) and 7.27–7.40 (17H, m); m/z (FAB, +ve ion, thioglycerol) 878 (MNa$^+$), b) 4-Methoxybenzyl (6R,7S)-7-[2-(2-aminothiazol-4-yl)-2-(Z)-hydroxyiminoacetamido]-3-[(2S)-tetrahydrofuran-2-yl]-1-carba-1-dethiaceph-3-em-4-carboxylate To a solution of 4-methoxybenzyl (6R,7S)-7-[2-(2-tritylaminothiazol-4-yl)-2-[(Z)-2-methoxyprop-2-yloxyimino]acetamido]-3-[(2S)-tetrahydrofuran-2-yl]-1-carba-1-dethiaceph-3-em-4-carboxylate (160 mg, 0.18 mmol) in dichloromethane (1.5 ml) was added 80% acetic acid (4.4 ml) and the mixture stirred at 40° C. for 2h. The mixture was diluted with ethyl acetate and washed successively with water (×2), saturated aqueous sodium hydrogen carbonate (×2) and water, dried and then concentrated in vacuo. The residue was triturated with diethyl ether to yield the title compound (65 mg, 67%); $v_{max}$ (KBr) 3418, 3326, 1774, 1716, 1657, 1523 and 1386 cm$^{-1}$; $\delta_H$ (d$_6$-DMSO) 1.47–1.62 (2H,m), 1.74–2.08 (4H, m), 2.25–2.35 (2H, m), 3.63–3.87 (3H, m), 3.75 (3H, s), 4.68 (1H, m), 5.13 (2H, s), 5.45 (1H, dd, J 8.7, 5.1 Hz), 6.67 (1H, s), 6.92 (2H, d, J 8.6 Hz), 7.12 (2H, br. s, exch.), 7.36 (2H, d, J 8.6 Hz), 9.10 (1H, d, J 8.7 Hz) and 11.28 (1H, s, exch.); m/z (CI, +ve ion, ammonia) 542 (MH$^+$).

c) Sodium (6R,7S)-7-[2-(2-aminothiazol-4-yl)-2-(Z)-hydroxyiminoacetamido]-3-[(2S)-tetrahydrofuran-2-yl]-1-carba-1-dethiaceph-3-em-4-carboxylate A solution of 4-methoxybenzyl (6R, 7S)-7-[2-(2-aminothiazol-4-yl)-2-(Z) hydroxyiminoacetamido]-3-[(2S)-tetrahydrofuran-2-yl]-1-carba-1-dethia-ceph-3-em-4-carboxylate (65 mg, 0.12 mmol) in dichloromethane (10 ml) was added to a solution of aluminium chloride (48 mg, 0.36 mmol) in anisole (2 ml) and dichloromethane (1 ml) as described in Example 1(n). After quenching with trisodium citrate (0.5M, 3.7 ml) and subsequent work-up, the product was purified by chromatography on HP20SS eluting with water, then 2% THF in water. Fractions containing the product (h.p.l.c. analysis) were combined and freeze-dried to give the title compound (14 mg, 26%); $v_{max}$ (KBr) 1741, 1593, 1531, 1407 and 1335 cm$^{-1}$; $\delta_H$ (d$_6$-DMSO) 1.39–1.53 (2H, m), 1.71–1.90 (3H, m), 2.02–2.13 (3H, m), 3.52–3.80 (3H, m), 4.94 (1H, dd, J 7.8, 7.4 Hz), 5.25 (1H, dd, J 8.1, 5.0 Hz), 6.73 (1H, s), 7.18 (2H, br.s, exch.) and 11.51 (1H, br.s, exch.).

EXAMPLE 6

Sodium (6R,7S)-7-[2-(2-aminothiazol-4-yl)-2-(Z)-difluoromethoxyiminoacetamido]-3-[(2S)-tetrahydrofuran-2-yl]-1-carba-1-dethiaceph-3-em-4-carboxylate 2-(2-Aminothiazol-4-yl)-2-(Z)-difluoromethoxyiminoacetic acid (34 mg, 0.14 mmol) in DMF (2 ml) was treated with methanesulphonyl chloride (11 μl, 0.14 mmol) and N,N-diisopropylethylamine (25 μl, 0.14 mmol) as described in Example 1(m). This was then treated successively with a solution of 4-methoxybenzyl (6R,7S)-7-amino-3-[(2S)-tetrahydrofuran-2-yl]-1-carba-1-dethiaceph-3-em-4-carboxylate (45 mg, 0.12 mmol) in DMF (2 ml) and pyridine (12 μl, 0.14 mmol). After work-up the product was purified by chromatography on silica gel eluting with 30,50 and 70% ethyl acetate in hexane to yield the title compound as a colourless foam (50 mg, 71%); $v_{max}$ ($CH_2Cl_2$) 3400, 1754, 1718, 1685, 1613, 1532 and 1516 cm$^{-1}$; $\delta_H$ ($CDCl_3$) 1.51–2.52 (8H, m), 3.78–3.97 (3H, m), 3.81 (3H, s), 4.96 (1H, dd, J 8.6, 7.0 Hz), 5.17 (2H, s), 5.63 (1 H, dd, J 7.9, 4.9 Hz), 5.93 (2H, br.s, exch.), 6.59 (1H, dd, J 73.9, 70.8 Hz), 6.88 (2H, d, J 8.7 Hz) 6.90 (1H, s), 7.33 (2H, d, J 8.7 Hz) and 8.54 (1H, d, J 7.9 Hz); m/z (CI, +ve ion, ammonia) 592 (MH$^+$).

b) Sodium (6R,7S)-7-[2-(2-aminothiazol-4-yl)-2-(Z)-difluoromethoxyiminoacetamido]-3-[(2S)-tetrahydrofuran-2-yl]-1-carba-1-dethiaceph-3-em-4-carboxylate A solution of 4-methoxybenzyl (6R,7S)-7-[2-(2-aminothiazol-4-yl)-2-(Z)-difluoromethoxyiminoacetamido]-3-[(2S)-tetrahydrofuran-2-yl]-1-carba-1-dethiaceph-3-em-4-carboxylate (46 mg, 0.078 mmol) in dichloromethane (3 ml) was added to a solution of aluminium chloride (31 mg, 0.23 mmol) in anisole (1.4 ml) and dichloromethane (0.7 ml) as described in Example 1(n). After quenching with trisodium citrate (0.5M, 2.4 ml) and subsequent work-up, the product was purified by chromatography on HP20SS eluting with water, then 1,2,4 and 5% THF in water. Fractions containing the product (h.p.l.c. analysis) were combined and freeze-dried to give the title compound (25 mg, 65%); $v_{max}$ (KBr) 1749, 1670, 1595, 1534 and 1388 cm$^{-1}$; $\delta_H$ ($d_6$-DMSO) 1.40–1.52 (2H, m), 1.73–1.89 (3H, m), 2.01–2.11 (3H, m), 3.55–3.80 (3H, m), 4.92 (1H, dd, J 8.6, 6.8 Hz), 5.24 (1H, dd, J 8.3, 4.9 Hz), 6.99 (1H, s), 7.13 (1H, t, J 71.4 Hz), 7.36 (2H, br.s, exch.) and 9.52 (1H, d, J 8.3 Hz); m/z (FAB, +ve ion, thioglycerol) 494 (MH$^+$), 516 (MNa$^+$).

We claim:

1. A compound of formula (I) or a salt or pharmaceutically acceptable in vivo hydrolysable ester thereof:

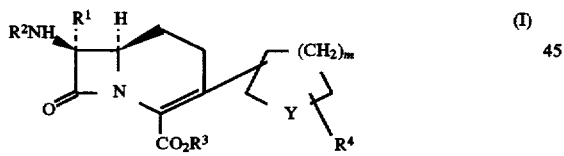

wherein:

$R^1$ is hydrogen, methoxy or formamido;

Y is O, S, SO or $SO_2$ and m is 1 or 2;

$R^2$ is an acyl group of the formulae (a)–(f):

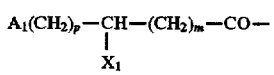  (a)

$A_2CO-$  (b)

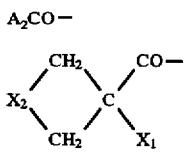  (c)

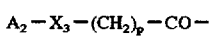  (d)

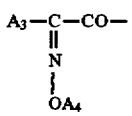  (e)

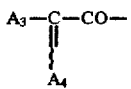  (f)

wherein p is 0, 1 or 2; m is 0, 1 or 2; $A_1$ is ($C_{1-6}$)alkyl, substituted ($C_{1-6}$)alkyl wherein the substituents are the same as for $R^4$ below, ($C_{3-6}$)cycloalkyl, cyclohexenyl, cyclohexadienyl, an aryl or heteroaryl group, a ($C_{1-6}$) alkylthio group or ($C_{1-6}$)alkyloxy; $X_1$ is a hydrogen or halogen atom, a carboxylic acid, carboxylic ester, sulphonic acid, azido, tetrazolyl, hydroxy, acyloxy, amino, ureido, acylamino, a heterocyclyamino selected from 2-amino thiazole, amino quinoline, amino indole, amino pyrazole or 3-amino pyrrole, guanidino or acylureido; $A_2$ is an aryl group; a substituted ($C_{1-6}$)alkyl group; or a substituted dithietane; $X_2$ is a $-CH_2OCH_2-$, $-CH_2SCH_2-$ or ($C_{2-6}$)alkylene group; $X_3$ is an oxygen or sulphur atom; $A_3$ is an aryl or heteroaryl group; and $A_4$ is hydrogen, ($C_{1-6}$)alkyl, ($C_{3-8}$)cycloalkyl, ($C_{3-8}$)cycloalkyl($C_{1-6}$)alkyl, ($C_{1-6}$) alkoxycarbonyl($C_{1-6}$)alkyl, ($C_{2-6}$)alkenyl, carboxy ($C_{1-6}$)alkyl, ($C_{2-6}$)alkynyl, aryl or ($C_{1-6}$)alkyl substituted by up to three aryl groups;

$CO_2R^3$ is a carboxy group or a carboxylate anion, or $R^3$ is a readily removable carboxy protecting group or a pharmaceutically acceptable salt-forming group or in vivo hydrolysable ester group;

$R^4$ represents hydrogen or up to four substituents, which may be present on any of the carbon atoms in the ring system shown, selected from ($C_{1-6}$)alkyl, ($C_{2-6}$)alkenyl, ($C_{2-6}$)alkynyl, ($C_{1-6}$)alkoxy, hydroxy, halogen, amino, ($C_{1-6}$)alkylamino, acylamino, ($C_{1-6}$)dialkylamino, $CO_2R$, $CONR_2$, $SO_2NR_2$ where R is hydrogen or ($C_{1-6}$)alkyl or which may be the same or different and wherein any $R^4$ ($C_{1-6}$)alkyl substituent is optionally substituted by one or more substituents selected from the list from which $R^4$ is selected;

wherein "aryl" is phenyl or naphthyl, each optionally substituted with up to five groups selected from the group consisting of halogen, mercapto, ($C_{1-6}$)alkyl, phenyl, ($C_{1-6}$)alkoxy, hydroxy($C_{1-6}$)alkyl, mercapto ($C_{1-6}$)alkyl, halo($C_{1-6}$)alkyl, hydroxy, amino, nitro, carboxy, ($C_{1-6}$)alkylcarbonyloxy, ($C_{1-6}$) alkoxycarbonyl, formyl and ($C_{1-6}$)alkylcarbonyl groups; and "heteroaryl" is an aromatic heterocyclic ring or ring system, each ring having 5 or 6 ring atoms selected from furan, thiophene, pyrrole, oxazole, thiazole, imidazole, pyrazole, isoxazole, isothiazole, 1,2,3-oxadiazole, 1,2,3-triazole, pyridine, pyrimidine, pyrazine, indole, isoindole, benzamidazole, benzthiazole or quinolone.

2. A compound as claimed in claim 1 wherein $R^1$ is hydrogen.

3. A compound as claimed in claim 1 wherein the cyclic ether or thioether at the 3-position of the cephalosporin nucleus is unsubstituted or substituted by up to three substituents $R^4$, selected from ($C_{1-6}$)alkyl, ($C_{1-6}$)alkoxy, ($C_{1-6}$) alkoxycarbonyl ($C_{1-6}$)alkoxy ($C_{1-6}$)alkyl, and ($C_{1-6}$) alkanoyloxy($C_{1-6}$)alkyl.

4. A compound as claimed in claim 1 wherein m is 1.

5. A compound of claim 1 selected from:

Pivaloyloxymethyl (6R,7S)-7-[2-(2-aminothiazol-4-yl)-2-(Z)-methoxyiminoacetamido]-[(S)-tetrahydrofuran-2-yl]-1-carba-1-dethiaceph-3-em-4-carboxylate, sodium (6R,7S)-7-[2-(2-aminothiazol-4-yl)-2-(Z)-methoxyiminoacetamido]-3-[(S)-tetrahydrofuran-2-yl]-1-carba-1-dethiaceph-3-em-4-carboxylate, 4-Methoxybenzyl (6R,7S)-7-phenylacetamido-3-[(R and S)-tetrahydrofuran-2-yl]-1-carb-1-dethiaceph-3-em-4-carboxylate, 4-Methoxybenzyl (6R,7S)-7-phthalimido-3-[(S)-tetrahydrofuran-2-yl]-1-carba-1-dethiaceph-3-em-4-carboxylate, sodium (6R,7S)-7-[2-(2-aminothiazol-4-yl)-2-(Z)-prop-2-yloxyiminoacetamido]-3-[(2S)-tetrahydrofuran-2-yl]-1-carba-1-dethiaceph-3-em-4-carboxylate, 4-Methoxybenzyl (6R,7S)-7-[2-(2-aminothiazol-4-yl)-2-(Z)-prop-2-yloxyiminoacetamido]-3-[(2S)-tetrahydrofuran-2-yl]-1-carba-1-dethiaceph-3-em-4-carboxylate, sodium (6R,7S)-7-[2-(2-aminothiazol-4-yl)-2-(Z)-hydroxyiminoacetamido]-3-[(2S)-tetrahydrofuran-2-yl]-1-carba-1-dethiaceph-3-em-4-carboxylate, 4-Methoxybenzyl (6R,7S)-7-[2-(2-aminothiazol-4-yl)-2-(Z)-hydroxyiminoacetamido]-3-[(2S)-tetrahydrofuran-2-yl]-1-carba-1-dethiaceph-3-em-4-carboxylate and sodium (6R,7S)-7-[2-(2-aminothiazol-4-yl)-2-(Z)-difluoromethoxyiminoacetamido]-3-[(2S)-tetrahydrofuran-2-yl]-1-carba-1-dethiaceph-3-em-4-carboxylate.

6. A pharmaceutical composition comprising a compound of claim 1 and a pharmaceutically acceptable carrier.

7. A compound of claim 1 or a pharmaceutically acceptable salt or in vivo hydrolysable ester thereof.

8. A method of treating bacterial infections in humans and animals which comprises the administration of a therapeutically effective amount of an antibiotic compound of claim 1 or a pharmaceutically acceptable in vivo hydrolysable ester thereof.

9. A compound as claimed in claim 1 wherein the cyclic ether or thioether at the 3-position of the cephalosporin nucleus is unsubstituted or substituted by up to three substituents $R^4$, selected from methyl, methoxy, methoxycarbonyl, methoxymethyl and acetoxymethyl.

10. A method of treating bacterial infections in humans and animals which comprises the oral administration of a therapeutically effective amount of an antibiotic compound of claim 1 or a pharmaceutically acceptable in vivo hydrolysable ester thereof.

* * * * *